US009684002B2

(12) United States Patent
Westerman et al.

(10) Patent No.: US 9,684,002 B2
(45) Date of Patent: Jun. 20, 2017

(54) MARKERS FOR ACUTE KIDNEY INJURY

(75) Inventors: Mark E. Westerman, San Diego, CA (US); Rinaldo Bellomo, Ivanhoe (AU); John Prowle, London (GB); Michael Brownstein, Rockville, MD (US)

(73) Assignees: INTRINSIC LIFESCIENCES LLC, LaJolla, CA (US); AUSTIN HEALTH, Victoria (AU)

( * ) Notice: Subject to any disclaimer, the term of this patent is extended or adjusted under 35 U.S.C. 154(b) by 786 days.

(21) Appl. No.: 13/697,313

(22) PCT Filed: May 10, 2011

(86) PCT No.: PCT/US2011/035944
§ 371 (c)(1),
(2), (4) Date: Jan. 30, 2013

(87) PCT Pub. No.: WO2011/143232
PCT Pub. Date: Nov. 17, 2011

(65) Prior Publication Data
US 2013/0130287 A1 May 23, 2013

Related U.S. Application Data

(60) Provisional application No. 61/333,112, filed on May 10, 2010.

(51) Int. Cl.
*G01N 33/70* (2006.01)
*G01N 33/68* (2006.01)
*G01N 33/74* (2006.01)

(52) U.S. Cl.
CPC ......... *G01N 33/70* (2013.01); *G01N 33/6893* (2013.01); *G01N 33/74* (2013.01); *G01N 2333/705* (2013.01); *G01N 2800/347* (2013.01); *G01N 2800/60* (2013.01)

(58) Field of Classification Search
CPC .... G01N 33/70; G01N 33/6893; G01N 33/74; G01N 2333/705; G01N 2800/347; G01N 2800/60
See application file for complete search history.

(56) References Cited

U.S. PATENT DOCUMENTS

2007/0224186 A1 9/2007 Kulaksiz et al.
2008/0014604 A1* 1/2008 Devarajan .......... G01N 33/6893 435/23
2009/0215095 A1 8/2009 Lauth et al.

FOREIGN PATENT DOCUMENTS

WO WO2008/113363 A1 * 9/2008 ............. G01N 33/68

OTHER PUBLICATIONS

EP Application No. 11781153.9-1408, International Search Report, dated Nov. 7, 2013.

Ho Julie et al, "Mass spectrometry-based proteomic analysis of urine in acute kidney injury following cardiopulmonary bypass: a nested case-control study.", American Journal of Kidney Diseases: The Official Journal of the National Kidney Foundation Apr. 2009, vol. 53, No. 4, Apr. 2009 (Apr. 2009), pp. 584-595.
Malyszko J et al, "A Possible Role of Hepcidin in the Pathogenesis of Anemia Among Kidney Allograft Recipients", Transplantation Proceedings, Elsevier Inc, Orlando, FL; US, vol. 41, No. 8, Oct. 1, 2009 (Oct. 1, 2009), pp. 3056-3059.
Malyszko J et al, "Neutrophil Gelatinase-Associated Lipocalin Is a New and Sensitive Marker of Kidney Function in Chronic Kidney Disease Patients and Renal Allograft Recipients", Transplantation Proceedings, Elsevier Inc, Orlando,FL; US, vol. 41, No. 1, Jan. 1, 2009(Jan. 1, 2009), pp. 158-161.
Sangeeta Hingorani et al, "Ironing Out the Pathogenesis of Acute Kidney Injury", American Journal of Kidney Diseases, vol. 53, No. 4, Apr. 1, 2009(Apr. 1, 2009), pp. 569-571.
Ganz et al., "Immunoassay for human serum hepcidin" Blood, 2008, vol. 112, pp. 4292-4297.
Haase-Fielitz et al., "The predictive performance of plasma neutrophil gelatinase-associated lipocalin (NGAL) increases with grade of acute kidney injury", Nephrol. Dial. Transplant, 2009, vol. 24, pp. 3349-3354.
International Search Report in PCT/US2011/035944.
Bellomo, et al., Acute Renal Failure—Definition, Outcome Measures, Animal Models, Fluid Therapy and Information Technology Needs: The Second International Consensus Conference of the Acute Dialysis Quality Initiative (ADQI) Group, *Crit. Care*, vol. 8, pp. 204-212 (2004).
Uchino, et al., "Acute Renal Failure in Critically Ill Patients," *JAMA*, vol. 294, pp. 813-818 (2005).
Takami, et al. Effect of Surface Roughness on Hemolysis in a Pivot Bearing Supported Gyro Centrifugal Pump (C1E3), *Artificial Organs*, vol. 20, pp. 1155-1161 (1996).
Vercaemst, "Hemolysis in Cardiac Surgery Patients Undergoing Cardiopulmonary Bypass: A Review in Search of a Treatment Algorithm," *J. Extracorporeal Technology*, vol. 40, pp. 257-267 (2008).
Laarakkers, et al., "Hepcidin Levels in Acute Kidney Injury following Cardiopulmonary Bypass Grafting," *American Journ. of Kidney Disease*, vol. 54, pp. 979- (2009).
Nemeth, et al., "IL-6 Mediates Hypoferremia of Inflammation by Inducing the Synthesis of the Iron Regulatory Hormone Hepcidin," *Journ, of Clin. Investigation*, vol. 113, pp. 1271-1276 (2004).

(Continued)

*Primary Examiner* — Andrea S Grossman
(74) *Attorney, Agent, or Firm* — Foley & Lardner LLP

(57) ABSTRACT

Provided are methods and compositions for predicting the development of kidney disease, including acute kidney injury. In certain aspects and embodiments the provided methods and compositions are particularly useful for predicting kidney injury following an event likely to cause kidney injury and/or kidney failure in a patient, such as a cardiac surgery, e.g., a surgery involving a cardiopulmonary bypass (CPB), such as a coronary artery bypass graft surgery. In some embodiments, the higher the urinary hepcidin-to-urinary creatinine ratio (uHep/uCr) at 6-24 hours following initiation of CPB, the lower is the risk for development of AKI determined by RIFLE criteria in the ensuing four to five days. Conversely, the higher the urinary NGAL to urinary creatinine ratio (uNGAL/uCr) at 6-24 hours following initiation of CPB, the higher is the risk of developing CPB-mediated AKI over the same time period.

14 Claims, 11 Drawing Sheets

(56) References Cited

OTHER PUBLICATIONS

Kemna et al., "Time-Course Analysis of Hepcidin, Serum Iron, and Plasma Cytokine Levels in Humans Injected with LPS," *Blood*, vol. 106, pp. 1864-1866 (2005).
Park et al., "Hepcidin, a Urinary Antimicrobial Peptide Synthesized in the Liver," *Journ. of Biological Chemistry*, vol. 276, pp. 7806-7810 (2001).
Nemeth, et al., "Hepcidin Regulates Cellular Iron Efflux by Binding to Ferroportin and Inducing Its Internalization," *Science*, vol. 306, pp. 2090-2093 (2004).
Youden, "Index for Rating Diagnostic Tests," *Cancer*, vol. 3, pp. 32-35 (1950).
Swinkels et al., "Advances in Quantitative Hepcidin Measurements by Time-of-Flight Mass Spectrometry," *PLos One*, vol. 3, No. 7, e2706 (2008).
Pepe, "Combining Diagnostic Test Results to Increase Accuracy," *Biostatistics*, vol. 1, pp. 123-140 (2000).

\* cited by examiner

| RIFLE CLASS | % Change From | | |
|---|---|---|---|
| | Baseline-6 hours | 6-24 hours | Baseline-24 hours |
| No AKI | 849.28 | 37.52 | 1205.11 |
| R | 745.66 | 71.92 | 1353.83 |
| No AKI & R | 840.76 | 31.25 | 1134.82 |
| I | 1384.89 | -34.72 | 415.51 |
| F | 1126.28 | -35.96 | 801.92 |
| I & F | 931.24 | -37.95 | 537.08 |

Figure 5 delta uHep/uCr delta uNGAL/uCr 6 hours AKI R

Figure 6 delta uHep/uCr delta uNGAL/uCr 24 hrs RIFLE I

Figure 10
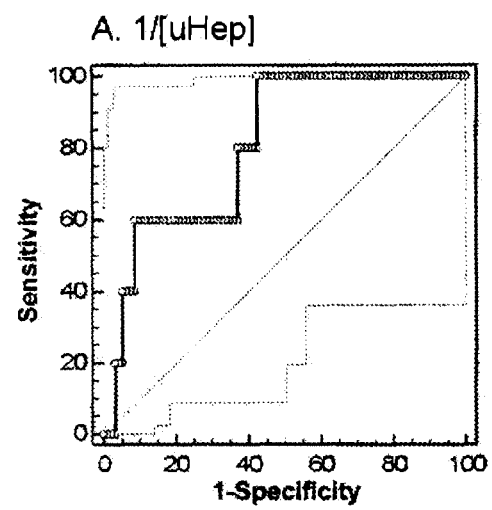
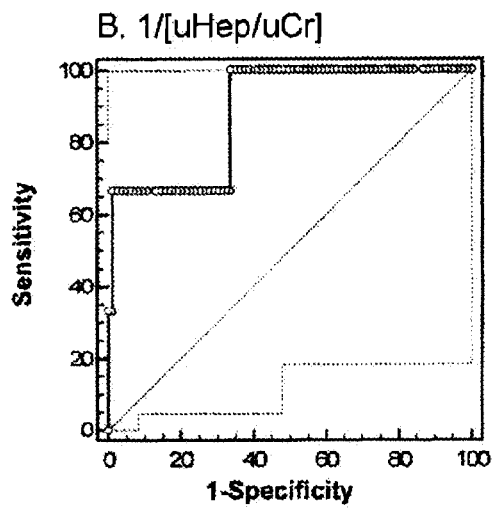
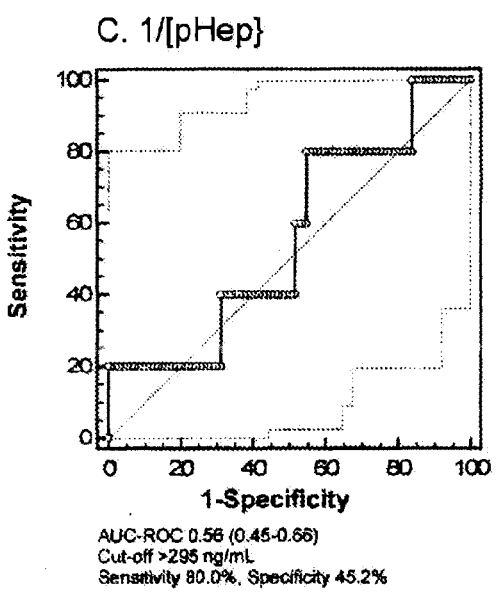

Lateral flow device

MARKERS FOR ACUTE KIDNEY INJURY

FIELD OF THE INVENTION

This description relates to methodology and compositions for predicting and/or diagnosing kidney injury.

BACKGROUND OF THE INVENTION

Acute Renal Failure (ARF) is said to occur in anywhere from 1% to 25% of critically ill patients and mortality in these populations ranges from 28% to 90%. Most definitions of ARF have common elements, including the use of serum creatinine and urine volume. Although the kidney has numerous functions, these are the only functions that are routinely and easily measured and that are unique to the kidney. The accuracy of a creatinine clearance measurement even under the best circumstances is limited because as glomerular filtration rate (GFR; a measure of kidney function) falls creatinine secretion is increased, and thus the rise in serum creatinine is attenuated.

Thus, creatinine excretion is much greater than the actual filtered urine load, resulting in a potentially large overestimation of the GFR (as much as a twofold difference) and erroneous assumptions regarding kidney function by clinicians. In addition, plasma creatinine concentrations only rise if greater than 50% of the normal GFR is lost, making GFR an unreliable and very insensitive marker of kidney failure and causing delays in diagnosis well beyond 24 hours post-surgery. Nevertheless, serum creatinine remains the key kidney-specific biomarker used to determine whether renal function is improving, declining, or stabilizing. Like creatinine clearance, the serum creatinine will not be an accurate reflection of GFR in the non-steady-state condition of ARF. Urine output is far less specific than serum creatinine for determination of kidney function, except when urine output is severely decreased or absent. Severe ARF can exist despite normal urine output (i.e., nonoliguric) but changes in urine output can occur long before biochemical changes are apparent.

The wide variety of definitions of ARF used in clinical practice in the past led to the formation of the Acute Dialysis Quality Initiative (ADQI) workgroup and publication of a consensus definition based on RIFLE criteria which are based solely on changes in serum creatinine and urine output. The RIFLE criteria allow for three classifications of increasing severity of kidney injury, including Risk, Injury, and Failure, and two outcome criteria, Loss, and End Stage Renal Disease or ESRD (Bellomo R., et al., 2004 Crit. Care 8: 204-12). The efficacy of the RIFLE criteria have been examined and shown to be a useful classification system for classifying kidney injury (Uchino S, et al., 2005, JAMA 294: 813-18).

Acute kidney injury (AKI) is a common and severe complication in hospitalized patients and is associated with increased morbidity and mortality. Cardiac disease and cardiac surgery are both common causes of AKI. In critically ill patients cardiac surgery with cardiopulmonary bypass (CPB) is the second most common cause of AKI. This condition can be classified as a form of cardiorenal syndrome (CRS) type 1, characterized by an abrupt worsening of renal function secondary to acute cardiac disease or procedures. Cardiac surgery associated AKI is a particular type of type 1 CRS for which no clear understanding of pathogenesis exists and no proven, effective prophylaxis or treatment is yet identified. Furthermore, existing renal markers, which confirm loss of renal function in this setting, are only very late markers, for the diagnosis of AKI late in the course of the problem.

SUMMARY OF THE INVENTION

Acute kidney injury (AKI) is seen following a number of surgical procedures, especially those that require the use of a heart-lung machine or "pump". These include Coronary Artery Bypass Grafts (CABG), cardiac valve replacements, aortic aneurism repairs, and organ transplants. Certain patients, such as elderly men and women, diabetics, and people with renal disease, have an especially high risk of developing AKI postoperatively.

Heretofore there has been no way to diagnose and, hence, to treat AKI quickly in the postoperative period. Several novel biomarkers have emerged recently that appear to have good sensitivity and specificity for the prediction of AKI after cardiopulmonary bypass (CPB) for cardiac surgery, and that may allow for CPB-associated AKI to be detected more rapidly than in the past. Furthermore, illuminating the basis of the physiological roles of these biomarkers, as well as their response to CPB and to other cardiac interventions, offers an opportunity not only to expand our understanding of the pathogenesis of CPB-associated AKI but also possibly to develop diagnostics and medical devices that will address the shortcomings of existing methods for detecting the presence and severity of AKI during and following CPB. Development of early biomarkers for ensuing CPB-associated AKI also could enable development of drugs and therapeutic interventions for AKI, few of which exist currently.

The present description addresses the critical deficiency of current biomarkers and methodology for early detection of AKI in CPB patients. Thus, the description encompasses methods and compositions for predicting or diagnosing kidney injury and/or AKI. Pursuant to various aspects and embodiments of the inventions, such methods and compositions may be used to predict AKI in a patient following an event likely to cause kidney damage or kidney failure.

In some embodiments such an event is a surgery, for example, a cardiac surgery such as a CPB surgery including CABG (coronary artery bypass graft) surgery. In some embodiments, the levels of hepcidin in a sample from the patient are measured and used as a predictor of kidney injury and/or AKI. In certain embodiments the hepcidin is hepcidin 1, in other embodiments the hepcidin is hepcidin 2, in other embodiments the hepcidin is hepcidin 3 and in yet other embodiments both hepcidin 1 and 2 are measured; in other embodiments hepcidin 1 and 3 are measured; in other embodiments hepcidin 2 and 3 are measured; and in yet another embodiment hepcidin 1 and 2 and 3 are measured simultaneously. The sample may be any biological sample from a patient, e.g., urine, blood, serum, or plasma. In various embodiments of the inventive methodology, measuring, detecting or determining the level of a biomarker or analyte as disclosed, e.g., hepcidin, may involve obtaining a biological sample from a patient and performing an appropriate assay on the sample to detect and or measure the biomarker; such assays may include steps such as extracting the biomarker or analyte from the sample, and/or adding necessary reagents, antibodies to the sample and/or other steps to prepare the sample for the detection or measurement steps of the assay.

In keeping with certain aspects and embodiments of this invention, development of kidney injury and predictions of kidney injury and/or AKI are determined by RIFLE criteria.

In instances where it is predicted that a patient is at risk of kidney injury or AKI, the inventive methodology may further involve an intervention to appropriately treat the patient, or a recommendation for a physician to appropriately treat the patient, or instructions to appropriately treat the patient; or an identification of the patient as being at risk of kidney injury or AKI. Possible interventions for patients with kidney injury or AKI include intravenous loading of sodium bicarbonate, followed by a continuous infusion of sodium bicarbonate, dialysis, continuous hemofiltration, drugs that inhibit local inflammation and tissue damage, or other interventions to treat the kidney or symptoms associated with kidney injury or AKI.

While the instant disclosure generally refers to a surgery, such as cardiac surgery, e.g., a CPB surgery including CABG, as an event likely to cause kidney damage or kidney failure, the methods and compositions of the invention can be applicable to any event associated with or likely to cause kidney injury and/or kidney failure, including any of various surgeries (e.g., heart, heart-lung, lung, liver, kidney, and transplant surgeries, especially where CPB is used); exposure to chemicals, pesticides, and/or toxins; burns including severe burns; and the like.

As used in this description, "uHep" means urinary hepcidin levels, "sHep" means serum hepcidin levels, "pHep" means plasma hepcidin, "uCr" means urinary creatinine levels, "sCr" means serum creatinine levels, "pCr" means plasma creatinine levels. As used in this description sHep and pHep are analogous as the authors have shown previously that sHep and pHep are highly correlated and equivalent.

In one aspect, provided is a method for predicting kidney disease following cardiopulmonary bypass (CPB) surgery. The method may include measuring urine hepcidin (uHep) and urinary creatinine (uCr) a patient following cardiopulmonary bypass (CPB) surgery and using the uHep and uCR ratio as a predictor of the development of acute kidney injury (AKI) in the patient.

In another aspect, a method is provided for predicting kidney disease following an event likely to cause kidney injury and/or failure in a patient. The method may include measuring urine hepcidin (uHep) and urinary creatinine (uCr) and using the kinetics of the change in uHep/uCr ratio following the event to predict development of AKI in the patient. In some embodiments a positive percent (%) change is associated with less severe RIFLE R AKI or no AKI and a negative percent (%) change in uHep/uCR is predictive of more severe RIFLE I and RIFLE F AKI after the event.

In another aspect, provided is a method for predicting kidney disease following an event likely to cause kidney injury and/or failure in a patient that involves measuring urine hepcidin (uHep) and urinary creatinine (uCr) and using the kinetics of the uHep/uCr ratio and the urinary NGAL (uNGAL; ng per milliliter of urine) to uCr ratio (uNGAL/uCr) following the event to predict development of AKI in the patient.

In another aspect, a method for is provided predicting kidney disease following an event likely to cause kidney injury and/or failure in a patient that involves measuring serum or plasma hepcidin (sHep) and serum creatinine (sCr) in the patient following said event and using said (sHep) and (sCr) to predict development of AKI in said patient.

In another aspect, provided is a method for predicting kidney disease following an event likely to cause kidney injury and/or failure in a patient that involves measuring urine hepcidin (uHep), serum or plasma hepcidin (sHep), urinary creatinine (uCr) and serum creatinine (sCr) in the patient following the event and using the kinetics of the uHep/uCr to sHep ratio to predict development of AKI in the patient.

In another aspect, a method is provided for predicting kidney disease in a patient following an event likely to cause kidney injury and/or failure in a patient that involves measuring serum hepcidin (sHep), serum creatinine (sCr) and serum NGAL (sNGAL) in said patient following the event and using the kinetics of change in sHep and sNGAL/sCr to predict development of AKI as determined by RIFLE criteria.

In another aspect, provided is a method for predicting kidney disease in a patient following an event likely to cause kidney injury and/or failure in a patient that involves measuring serum hepcidin (sHep), urinary creatinine (uCr) and urinary NGAL (sNGAL) in the patient following the event and using the kinetics of change of sHep and uNGAL/uCr to predict development of AKI in the patient.

In another aspect, a method is provided for predicting kidney disease in a patient following an event likely to cause kidney injury and/or failure in a patient involving measuring urinary hepcidin (uHep), urinary creatinine (uCR), serum creatinine (sCr) and serum NGAL (sNGAL) in the patient following the event and using the kinetics of sNGAL/sCr and uHep/uCr to predict development of AKI.

In various embodiments of the methods described here, the hepcidin, creatinine and/or NGAL is measured at about 3-9 hours; or about 4-8 hours; or about 5-7 hours; or about 6-24 hours; or about 6-12 hours; or about 8-12 hours; or about 6 hours; or about 7 hours; or about 8 hours; or about 9 hours; or about 10 hours; or about 11 hours; or about 12 hours; or about 13 hours; or about 14 hours; or about 16 hours; or about 18 hours; or about 20 hours; or about 22 hours; or about 24 hours after the event or the initiation of surgery. In some embodiments the hepcidin, creatinine and/or NGAL is measured at about 3-9 hours after the event or the initiation of surgery. In some embodiments of the methods described here, the hepcidin, creatinine and/or NGAL is measured at about 4-8 hours after the event or the initiation of surgery. In some embodiments of the methods described here, the hepcidin, creatinine and/or NGAL is measured at about 5-7 hours after the event or the initiation of surgery. In some embodiments of the methods described here, the hepcidin, creatinine and/or NGAL is measured at about 6-24 hours after the event or the initiation of surgery. In some embodiments of the methods described here, the hepcidin, creatinine and/or NGAL is measured at about 6-12 hours after the event or the initiation of surgery. In some embodiments of the methods described here, the hepcidin, creatinine and/or NGAL is measured at about 8-12 hours after the event or the initiation of surgery. In some embodiments of the methods described here, the hepcidin, creatinine and/or NGAL is measured at about 6 hours after the event or the initiation of surgery. In some embodiments of the methods described here, the hepcidin, creatinine and/or NGAL is measured at about 8 hours after the event or the initiation of surgery. In some embodiments of the methods described here, the hepcidin, creatinine and/or NGAL is measured at about 12 hours after the event or the initiation of surgery. In some embodiments of the methods described here, the hepcidin, creatinine and/or NGAL is measured at about 24 hours after the event or the initiation of surgery.

In this description, "about" is employed in quantitative terms to denote a range of plus-or-minus 10%. Thus, "about 3%" would encompass 23-3.3% and "about 10%" would encompass 9-11%. Moreover, where "about" is used in conjunction with a quantitative term, it is understood that, in addition to the value plus or minus 10%, the exact value of the quantitative term also is contemplated and described. For instance, the term "about 3%" expressly contemplates, describes, and includes exactly 3%.

In one embodiment of the invention, a method is provided in which hepcidin in a patient's urine is measured (for example, it may be expressed as ng hepcidin per ml urine (uHep)) at about 3-9 hours; or about 4-8 hours; or about 5-7 hours; or about 6-24 hours; or about 6-12 hours; or about 8-12 hours; or about 6 hours; or about 7 hours; or about 8 hours; or about 9 hours; or about 10 hours; or about 11 hours; or about 12 hours; or about 13 hours; or about 14 hours; or about 16 hours; or about 18 hours; or about 20 hours; or about 22 hours; or about 24 hours after initiation of surgery (such as cardiac surgery, for example a CPB surgery including CABG). In one embodiment, a method is provided in which hepcidin in a patient's urine is measured (for example, it may be expressed as ng hepcidin per ml urine (uHep)) at about 6-12 hours after initiation of surgery (such as cardiac surgery, for example a CPB surgery including CABG). In one embodiment, a method is provided in which hepcidin in a patient's urine is measured (for example, it may be expressed as ng hepcidin per ml urine (uHep)) at about 6 hours after initiation of surgery (such as cardiac surgery, for example a CPB surgery including CABG). In such methods, lower uHep levels are used to predict a higher risk of severe AKI, including RIFLE F and may be used to determine whether a patient should therefore receive early dialysis or continuous hemofiltration prior to more advanced renal dysfunction developing with the understanding that early intervention with dialysis or continuous hemofiltration may be beneficial and that such patients would be identified within about 3 to about 24 hours after initiation of surgery as having a >90% chance of requiring dialysis or continuous hemofiltration.

In one embodiment, a method is provided in which hepcidin in a patient's urine is measured (for example, it may be expressed as ng hepcidin per ml urine (uHep)) before initiation of surgery (0 hours), and at about 3-9 hours; or about 4-8 hours; or about 5-7 hours; or about 6-24 hours; or about 6-12 hours; or about 8-12 hours; or about 6 hours; or about 7 hours; or about 8 hours; or about 9 hours; or about 10 hours; or about 11 hours; or about 12 hours; or about 13 hours; or about 14 hours; or about 16 hours; or about 18 hours; or about 20 hours; or about 22 hours; or about 24 hours after initiation of surgery (such as cardiac surgery, for example a CPB surgery including CABG). In one embodiment, a method is provided in which hepcidin in a patient's urine is measured (for example, it may be expressed as ng hepcidin per ml urine (uHep)) before initiation of surgery (0 hours), and at about 6-12 hours after initiation of surgery (such as cardiac surgery, for example a CPB surgery including CABG). In one embodiment, a method is provided in which hepcidin in a patient's urine is measured (for example, it may be expressed as ng hepcidin per ml urine (uHep)) before initiation of surgery (0 hours), and at about 6 hours after initiation of surgery (such as cardiac surgery, for example a CPB surgery including CABG). In such methods, lower uHep levels in post-surgery measurements are used to predict a higher risk of severe AKI, including RIFLE F and may be used to determine whether a patient should therefore receive early dialysis or continuous hemofiltration prior to more advanced renal dysfunction developing with the understanding that early intervention with dialysis or continuous hemofiltration may be beneficial and that such patients would be identified within about 3 to about 24 hours after initiation of surgery as having a >90% chance of requiring dialysis or continuous hemofiltration.

In some embodiments of the methods described here the uHep concentration (ng/mgCr) measured at 24 hours after the event or initiation of surgery is used to predict development of AKI. In some embodiments of the methods described here, no change or a decrease in uHep concentrations (ng/mgCr) between 6 hours and 24 hours; or between 8 and 12 hours after the event or initiation of surgery is used to predict development of RIFLE I or RIFLE F AKI in the patient. In some embodiments of the methods described here an increase in uHep concentration (ng/mgCr) between 6 hours and 24 following the event or initiation of surgery of >25% is used to predict development of RIFLE R or no kidney injury in the patient. In some embodiments of the methods described here an increase in uHep concentrations between 6 hours and 24 hours after the event or initiation of surgery of >35% is used to predict no kidney injury in the patient. In some embodiments of the methods disclosed here, the ratio of the change in uNGAL/uCr from post initiation of surgery to 24 hours to the change in uHep/uCr from post initiation of surgery to 24 hours is used to predict development of AKI in the patient. In some embodiments, a weighted linear combination of uHep/uCr and uNGAL/uCr is used with Receiver-operating characteristic (ROC) area under the curve analysis to predict development of AKI in the patient.

In some aspects and embodiments of the methods and compositions disclosed here, the hepcidin levels used in the methods to predict kidney failure are calculated and/or expressed as a ratio of a second biomarker; for example the hepcidin levels may be calculated and/or expressed as a ratio of creatinine levels in the same sample type (for example the hepcidin levels may be expressed as ng hepcidin per milliliter of urine divided by urinary creatinine expressed as mg/ml urine). In certain embodiments a biomarker and/or a second biomarker includes one or more of hepcidin, creatinine, NGAL, L-FABP, cystatin-C, Kim-1, α-GST, π-GST, ferritin, transferrin, % TSAT, hemojuvelin, or erythropoietin. For example a second biomarker may be urinary L-FABP, urinary cystatin-C, urinary Kim-1, serum hepcidin, serum ferritin, serum non-transferrin bound iron (NTBI), serum transferrin, % TSAT, serum hemojuvelin, or serum erythropoietin. In some embodiments urinary hepcidin is a first biomarker and a second biomarker includes one or more of serum creatinine, urinary creatinine, urinary L-FABP, urinary cystatin-C, urinary Kim-1, serum hepcidin, serum ferritin, serum NTBI, serum transferrin, % TSAT, serum hemojuvelin, or serum erythropoietin.

In some embodiments, the hepcidin levels used in the methods described here to predict risk of kidney injury and/or AKI are calculated and/or expressed as a ratio of uHep/uCr concentrations to sHep concentrations (with urinary levels and serum levels optionally calculated and expressed as a ratio of a second biomarker such as creatinine); for example the hepcidin levels may be expressed as the ratio of uHep/uCr to sHep or the ratio of uHep/uCr to sHep/sCr.

In certain embodiments, a method is provided in which where hepcidin and creatinine are measured in a urine sample from a patient before initiation of surgery (0 hours), and at about 3-9 hours; or about 4-8 hours; or about 5-7 hours; or about 6-24 hours; or about 6-12 hours; or about 8-12 hours; or about 6 hours; or about 7 hours; or about 8 hours; or about 9 hours; or about 10 hours; or about 11 hours; or about 12 hours; or about 13 hours; or about 14 hours; or about 16 hours; or about 18 hours; or about 20 hours; or about 22 hours; or about 24 hours after initiation of surgery (such as cardiac surgery, for example a CPB surgery including CABG). In one embodiment, a method is provided in which hepcidin and creatinine in a patient's urine are measured before initiation of surgery (0 hours), and at about 6-12 hours after initiation of surgery (such as cardiac surgery, for example a CPB surgery including CABG). In one embodiment, a method is provided in which hepcidin and creatinine in a patient's urine are measured before initiation of surgery (0 hours), and at about 6 hours after initiation of surgery (such as cardiac surgery, for example a CPB surgery including CABG). In these embodiments, lower uHep/uCr levels in post surgical measurements may be used to predict a higher risk of severe AKI, including RIFLE I and RIFLE F, and may be used to determine whether a patient therefore should receive early dialysis or continuous hemofiltration prior to development of more advanced renal dysfunction. This would be done with the understanding that early intervention with dialysis or continuous hemofiltration might be beneficial and that such patients would be identified within 3 to about 24 hours after initiation of surgery, as having a >90% chance of requiring dialysis or continuous hemofiltration.

In some embodiments, the provided methods may include taking more than one hepcidin measurement and using changes in hepcidin to predict kidney injury and/or AKI. For example, the method may involve taking a first sample and a second sample from a patient, where a decrease in hepcidin levels in the second sample as compared to the first sample is used to predict kidney injury or kidney failure (AKI) in the patient, and where no change in the hepcidin levels or an increase in hepcidin levels is used to predict a lower risk of kidney injury (RIFLE R) or no risk of kidney injury (AKI-free) in the patient. In some such embodiments, the first sample is taken from a patient prior to initiation of surgery, or about 3-9 hours; or about 4-8 hours; or about 5-7 hours; or about 6-12 hours; or about 8-12 hours after initiation of surgery (such as cardiac surgery, for example a CPB surgery including CABG), and the second sample is taken about 6-24 hours after initiation of surgery In some embodiments, a method is provided in which uHep, uCr, and urinary NGAL (uNGAL) are measured before initiation of surgery (0 hours), and at about 3-9 hours; or about 4-8 hours; or about 5-7 hours; or about 6-24 hours; or about 6-12 hours; or about 8-12 hours; or about 6 hours; or about 7 hours; or about 8 hours; or about 9 hours; or about 10 hours; or about 11 hours; or about 12 hours; or about 13 hours; or about 14 hours; or about 16 hours; or about 18 hours; or about 20 hours; or about 22 hours; or about 24 hours after initiation of surgery (such as cardiac surgery, for example a CPB surgery including CABG). In some embodiments, a method is provided in which uHep, uCr, and urinary NGAL (uNGAL) are measured before initiation of surgery (0 hours), and at about 6-12 hours after initiation of surgery (such as cardiac surgery, for example a CPB surgery including CABG). In some embodiments, a method is provided in which uHep, uCr, and urinary NGAL (uNGAL) are measured before initiation of surgery (0 hours), and at about 6 hours after initiation of surgery (such as cardiac surgery, for example a CPB surgery including CABG). In these embodiments, again, lower uHep/uCr in post-surgical measurements accompanied by higher NGAL levels at such times may be used to predict a higher risk of severe AKI, including RIFLE I or RIFLE F and may be used to determine whether a patient should therefore receive early dialysis or continuous hemofiltration prior to the development of more advanced renal dysfunction with the understanding that early intervention with dialysis or continuous hemofiltration may be beneficial and that such patients would be identified, within about 3 to about 24 hours after initiation of surgery as having a >90% chance of requiring dialysis or continuous hemofiltration.

In certain embodiments, a method is provided where urinary hepcidin is measured before initiation of surgery (0 hours), and at about 3-9 hours; or about 4-8 hours; or about 5-7 hours; or about 6-24 hours; or about 6-12 hours; or about 8-12 hours; or about 6 hours; or about 7 hours; or about 8 hours; or about 9 hours; or about 10 hours; or about 11 hours; or about 12 hours; or about 13 hours; or about 14 hours; or about 16 hours; or about 18 hours; or about 20 hours; or about 22 hours; or about 24 hours after initiation of surgery (such as cardiac surgery, for example a CPB surgery including CABG). In one embodiment, a method is provided in which hepcidin in a patient's urine is measured (for example, it may be expressed as ng hepcidin per ml urine (uHep)) before initiation of surgery (0 hours), and at about 6-12 hours after initiation of surgery (such as cardiac surgery, for example a CPB surgery including CABG). In one embodiment, a method is provided in which hepcidin in a patient's urine is measured (for example, it may be expressed as ng hepcidin per ml urine (uHep)) before initiation of surgery (0 hours), and at about 6 hours after initiation of surgery (such as cardiac surgery, for example a CPB surgery including CABG). In these embodiments, lower uHep levels in post-surgical measurements may be used to predict a higher risk of moderately severe AKI, including RIFLE R or RIFLE I and may be used to determine whether a patient should therefore receive protective intervention with intravenous loading of sodium bicarbonate followed by a continuous infusion of sodium bicarbonate to prevent development of or decreases the chance of proceeding to develop severe AKI in the form of RIFLE F which would require either dialysis or continuous hemofiltration.

In some embodiments, a method is provided where urinary hepcidin is measured together with urinary creatinine (uCr) before initiation of surgery (0 hours), and at about 3-9 hours; or about 4-8 hours; or about 5-7 hours; or about 6-24 hours; or about 6-12 hours; or about 8-12 hours; or about 6 hours; or about 7 hours; or about 8 hours; or about 9 hours; or about 10 hours; or about 11 hours; or about 12 hours; or about 13 hours; or about 14 hours; or about 16 hours; or about 18 hours; or about 20 hours; or about 22 hours; or about 24 hours after initiation of surgery (such as cardiac surgery, for example a CPB surgery including CABG). In one embodiment, a method is provided in which hepcidin and creatinine in a patient's urine are measured before initiation of surgery (0 hours), and at about 6-12 hours after initiation of surgery (such as cardiac surgery, for example a CPB surgery including CABG). In one embodiment, a method is provided in which hepcidin and creatinine in a patient's urine are measured before initiation of surgery (0 hours), and at about 6 hours after initiation of surgery (such as cardiac surgery, for example a CPB surgery including CABG). In these embodiments, lower uHep/uCr levels in post-surgical measurements may be used to predict a higher risk of moderately severe AKI, including RIFLE R or RIFLE I and may be used to determine whether a patient should therefore receive protective intervention with intravenous loading of sodium bicarbonate followed by a continuous infusion of sodium bicarbonate to prevent development of or decreases the chance of proceeding to develop severe AKI in the form of RIFLE F which would require either dialysis or continuous hemofiltration.

In other embodiments, a method is provided where uHep/uCr is measured together with uCr, and uNGAL before initiation of surgery (0 hours), and at about 3-9 hours; or about 4-8 hours; or about 5-7 hours; or about 6-24 hours; or about 6-12 hours; or about 8-12 hours; or about 6 hours; or about 7 hours; or about 8 hours; or about 9 hours; or about 10 hours; or about 11 hours; or about 12 hours; or about 13 hours; or about 14 hours; or about 16 hours; or about 18 hours; or about 20 hours; or about 22 hours; or about 24 hours after initiation of surgery (such as cardiac surgery, for example a CPB surgery including CABG). In some embodiments, a method is provided in which uHep, uCr, and urinary NGAL (uNGAL) are measured before initiation of surgery (0 hours), and at about 6-12 hours after initiation of surgery (such as cardiac surgery, for example a CPB surgery including CABG). In some embodiments, a method is provided in which uHep, uCr, and urinary NGAL (uNGAL) are measured before initiation of surgery (0 hours), and at about 6 hours after initiation of surgery (such as cardiac surgery, for example a CPB surgery including CABG). In these embodiments, lower uHep/uCreat and higher uNGAL levels in post-surgical measurements may be used to predict a higher risk of moderately severe AKI, including RIFLE R or RIFLE I and may be used to determine whether a patient should therefore receive protective intervention with intravenous loading of sodium bicarbonate followed by a continuous infusion of sodium bicarbonate to prevent development of or decreases the chance of proceeding to develop severe AKI in the form of RIFLE F which would require either dialysis or continuous hemofiltration.

In some aspects and embodiments, provided is a quantitative lateral flow device for determination of urine hepcidin levels. In some aspects and embodiments provided is automated kinetic intervention diagnostic device or Acute Kidney Injury Diagnostic Device (AKIDD) to rapidly predict CPB-mediated AKI by i) obtaining a urine sample containing hepcidin (and optionally one or more additional biomarkers) at defined timepoints following initiation of CPB-assisted surgery and delivering a known volume to a device containing a binding surface or a solution or a chemical solution or to a HPLC MS/MS or to another mass determining device, ii) causing the sample containing hepcidin to come in contact with an anti-hepcidin antibody coated on the surface in a pre-determined concentration, iii) causing a second anti-hepcidin antibody labeled with a detectable label such as an enzyme or ligand or a fluorescent molecule or colloidal gold, iv) delivering the binding surface or solution to a detector where the quantity of hepcidin is determined by comparison detector signal to the detector signal of standard reference solution containing a pre-determined quantity or concentration of synthetic or recombinant hepcidin, v) transmitting the detector signal or signals to Acute Kidney Injury Diagnostic Device Prognosis Investigator (AKIDDPI) software and calculating the quantity or concentration or number of molecules of hepcidin in the urine sample, vi) displaying the quantity or concentration or number of molecules or concentrations of isoforms or percentage of isoforms in the urine sample on an electronic screen device and, vii) storing the data provided to the screen device where the data is placed into a patient coded software program containing an algorithm or algorithms or OEM software programs, viii) obtaining a second urine sample at a timepoint between 1 minute and 10 minutes or between 10 minutes and 100 minutes or between 1 hour and 6 hours, or between 6 hours and 24 hours or between 24 hours and 120 hours, ix) causing the sample to undergo steps ii, iii, iv, v, vii, where the quantity or concentration or number of molecules or ratio of hepcidin, x) calculating the kinetics, or absolute value, percentage change in the biomarker or biomarkers, and xi) providing the data to the AKIDDPI software algorithm where the potential for the patient to develop AKI is determined.

BRIEF DESCRIPTION OF THE DRAWINGS

FIGS. 10A, 10B and 10C show predictive indices of hepcidin for NOT requiring post-operative renal replacement therapy (RRT) initiation. A) Urine hepcidin, B) Urine hepcidin/urine creatinine, C) Plasma hepcidin.

DETAILED DESCRIPTION OF THE PREFERRED EMBODIMENTS

Figure 1:
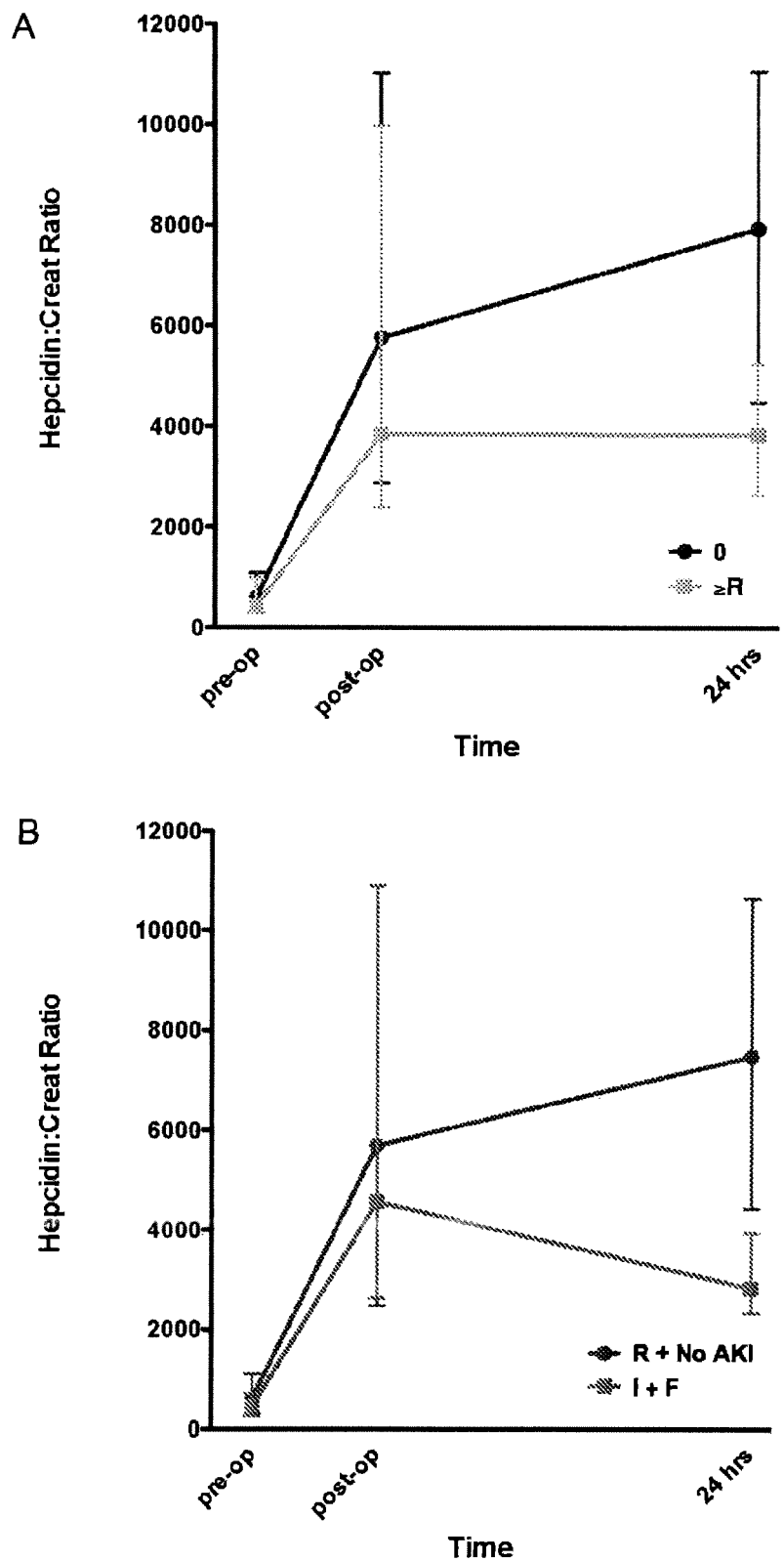
FIGS. 1A and 1B show post-operative changes in urinary hepcidin for patients with and without RIFLE R AKI.

Previous studies have shown that, when cardiac surgery is performed using CPB, there is injury to red cells and release of free hemoglobin (Takami Y., et al., 1996, Artificial Organs 20:1155-161). Aside from complete red blood cell fragmentation there also can be red cell damage, resulting in altered rheological properties. Increased levels of free red blood cell constituents together with an exhaustion of their scavengers transferrin and haptoglobin result in a variety of serious clinical sequelae, such as increased systemic vascular resistance, altered coagulation profile, platelet dysfunction, renal tubular damage, and increased mortality (Vercaemst L., 2008, J. Extracorporeal Technology 40: 257-67). Such injury raises concerns that CPB associated AKI may be a form of renal sideropathy and that free or inappropriately liganded iron related toxicity may play a role.

NGAL is a siderophore-binding lipocalin involved in ischemic renal injury and repair processes. Siderophores, first identified in bacteria, are proteins that have evolved to very efficiently scavage iron and other essential metals required for proliferation from the environment or their host. A human siderophore activity has been observed previously but to date has not been isolated. In normal health, NGAL is expressed at very low level in neutrophils and stimulated epithelia including kidney, heart, lung, trachea, liver, colon, stomach, and brain. Plasma NGAL in AKI appears to be derived from distal tubular back-leakage into the blood and from extra-renal sources as a result of organ cross-talk of the injured kidney. After glomerular filtration of NGAL, endocytosis via receptors such as megalinR/24p3R into proximal tubules or secretion with the urine may occur. Urinary NGAL (uNGAL) is derived from local synthesis in distal parts of the nephron after injury or by excessively filtered plasma NGAL.

Using an unbiased proteomics approach, Ho et al. (American Journal of Kidney Disease 53: 584-95, 2009) looked for proteins in the urine that might reflect underlying tubular injury. They enrolled 44 cardiac surgery patients in a nested cohort study and identified three biomarkers of renal damage after cardiac surgery—NGAL, hepcidin, and alpha-1 microglobulin. They used a semi-quantitative SELDI-TOF-MS assay of hepcidin, not a truly quantitative assay. Hepcidin, a central systemic regulator of iron homeostasis, was elevated in the urine of patients not developing AKI after cardiac surgery, although others have questioned the methodology and conclusions (Laarakkers, C. M., et al., 2009, American Journal of Kidney Disease 54: 979). Urinary hepcidin (uHep/uCr) has been shown to increase with inflammation and to decline as inflammation is resolved, due to its responsiveness to the inflammatory cytokine IL-6 (Nemeth, E., et al., 2004, Journal of Clinical Investigation 113: 1271-76; Kemna, E. H. J. M., et al., 2005, Blood 106: 1864-66).

Produced in the liver, the biologically active form of hepcidin is a peptide hormone that has a 25-amino acid sequence, Asp Thr His Phe Pro Ile Cys Ile Phe Cys Cys Gly Cys Cys His Arg Ser Lys Cys Gly Met Cys Cys Lys Thr (hepcidin-25; SEQ. ID No: 1), that circulates in plasma, and that is excreted in urine (Park, C. H., et al., 2001, Journal of Biological Chemistry 276: 7806-10). Two other hepcidin isomers, hepcidin-22 (Phe Pro Ile Cys Ile Phe Cys Cys Gly Cys Cys His Arg Ser Lys Cys Gly Met Cys Cys Lys Thr; SEQ. ID No:2) and hepcidin-20 (Pro Ile Cys Ile Phe Cys Cys Gly Cys Cys His Arg Ser Lys Cys Gly Met Cys Cys Lys Thr; SEQ. ID No:3) formed by deletions of three or five amino acids at the N-terminus of hepcidin-25 are also found in the serum and urine in lesser quantities in normal adults. The biological relevance of the hepcidin-22 and -20 isoforms is currently not clear. Hepcidin regulates plasma iron levels in response to changes in dietary and systemic iron load, anemia, hypoxia, inflammation, and infections. Hepcidin is an acute phase protein that is increased in inflammatory diseases by IL-6, an inflammatory cytokine and principal regulator of hepcidin during inflammation. Hepcidin's principal bioactivity is the rapid induction of hypoferremia. Injection of a single dose of synthetic hepcidin in mice causes a dramatic drop in serum iron within 1 hour that persisted for up to 72 hours.

Hepcidin inhibits cellular iron efflux by binding to ferroportin, the sole known iron exporter in humans, at the cell surface and inducing the ligand and receptor internalization and degradation (Nemeth, E., et al., 2004, Science 306: 2090-93). The iron channel, ferroportin, is found in all the tissues that export iron into plasma: basolateral membranes of duodenal enterocytes and the cell membranes of placental cells, hepatocytes and macrophages. In these locations, ferroportin is in a unique position to regulate the flow of iron into plasma from the diet, maternal sources, hepatic stores, and from macrophages engaged in recycling senescent erythrocytes. The homeostatic loop involving hepcidin and ferroportin maintain normal extracellular iron concentrations. Hepcidin production is increased by iron loading and when plasma transferrin saturation rises as a result of increased dietary iron intake, it acts as a stimulus for hepcidin production in hepatocytes. Under the influence of elevated hepcidin, ferroportin is internalized from the cell surface and degraded. Influx of iron into plasma from the duodenum, hepatocytes, and macrophages is decreased, and the small plasma iron pool is restored to normal by utilization of plasma iron for erythropoiesis. It is well-established that hepcidin is the master regulator of iron homeostasis and tissue iron distribution in vertebrates and essential for normal red blood cell production in humans. Hepcidin has emerged as a promising biomarker due to its direct involvement in the maintenance of normal iron homeostasis, which is dysregulated in a wide variety of genetic diseases, iron and hematological disorders, inflammatory diseases, chronic diseases, acute diseases, acute and chronic viral and bacterial infections, and cancers.

To examine the utility of hepcidin as a biomarker for AKI, urine and serum samples were obtained from patients enrolled in the Cardiopulmonary bypass, Renal injury and Atorvastatin Trial (CREAT—Clinicaltrials.Gov Nct00910221), a single center randomised controlled trial of peri- and post-operative atorvastatin vs. placebo for the prevention of AKI in higher risk patients undergoing CPB. In this study, statin therapy did not influence the incidence of post-operative AKI. The patients studied underwent elective cardiothoracic surgery with planned CPB. They were selected because they had ≥1 risk factor for post-operative AKI (age ≥70 years, New York Heart Association heart failure symptom severity class 3 or 4, left ventricular ejection fraction <35%, insulin-requiring diabetes mellitus, prior cardiac surgery, valvular surgery +/−coronary artery bypass, pre-operative creatinine >106.1 μmol/L). Exclusion criteria included emergency surgery, chronic kidney disease stage 5 and evidence of pre-operative AKI. Renal function was monitored for five days post-operatively.

AKI was defined based on the pre-operative-to-peak serum creatinine in the first 5 days post-operatively, using the creatinine criteria of the RIFLE consensus definition of AKI. Full information on post-operative serum creatinine was available, and this was deemed the most robust definition of clinically significant changes in renal excretory function. Primary definition of AKI was the occurrence of RIFLE class R or greater (a >50% rise in creatinine from baseline) in the five post-operative days. Additional analysis was performed to assess the ability of hepcidin to predict more severe renal dysfunction RIFLE class I or greater and RIFLE class F (>100% and >200% rise in creatinine from baseline respectively). Of the 100 patients randomized, 5 withdrew or had surgery rescheduled. In two patients full sets of serum and urine were not collected as a patient was unavailable for clinical reasons and thus, 93 sets of patient urine samples were available for analysis. Further, no frozen aliquots of serum remained after other pre-planned assays for 8 patients, thus analysis of serum hepcidin was performed in 85 patients.

Demographic and clinical data were collected pre-operatively and over the first 24 hours post-surgery. Serum and urine samples were obtained and creatinine and hepcidin were measured pre-operatively, on return to ICU (x=4.50 hr; 3.58-9.13 hr), and 24 hours (x=28.50 hr; 27.58-33.13 hr) after CPB. Creatinine was also measured daily for five days thereafter. Aliquots of serum and urine were frozen and stored at −70° C. immediately after collection and separation.

Fractional excretion (FE) of hepcidin, the proportion of filtered hepcidin that appears in urine was approximated by assuming that 100% of filtered creatinine is excreted in the urine using the formula:

$$FE = \frac{[\text{Hepcidin}]_{Urine} \cdot [\text{Creatinine}]_{Serum}}{[\text{Hepcidin}]_{Serum} \cdot [\text{Creatinine}]_{Urine}} \cdot 100\%.$$

Statistical analysis was performed using GraphPad Prism version 5.0a for Mac OS (GraphPad Software, La Jolla Calif. USA). Categorical data were reported as percentages with 95% confidence interval of the mean percentage, and compared using Fisher's exact test. Continuous data were reported as median with inter-quartile range (IQR) and compared using the Mann-Whitney U test, paired continuous data was compared using the Wilcoxon matched pairs test. Between-group comparison was performed using Kruskal-Wallis test with post-test comparison.

The ability of hepcidin to predict AKI was assessed by plotting receiver-operator characteristic (ROC) curves and reported as area under the curve (AUC) with 95% confidence intervals of the AUC and p value for significance deviation from the null model AUC of 0.5. For comparisons, statistical significance was denoted by two sided p values of <0.05. ROC curve optimal cut-off values for diagnosis, for curves with a statistically significant AUC, were defined as the point which maximized the Youden index, defined as (sensitivity+specificity)−1 (Youden W J, Cancer 1950; 32-5)

Of the patients in this study 25 of 93 developed AKI as defined by RIFLE≥R (27%). Fourteen patients developed RIFLE≥I AKI (15%) and 10 developed RIFLE=F (9.3%). Median and mean serum creatinine peaked on the third morning after cardio-pulmonary bypass. Of the 25 patients with RIFLE–R or greater AKI, 16 had achieved RIFLE–R by creatinine criteria (50% rise in serum creatinine) by post-operative day 1. Significantly, only 8 of 14 patients going on to develop RIFLE I or greater and only 5 of 10 developing RIFLE F satisfied creatinine criteria for RIFLE–R on post-operative day 1. Patient demographics, co-morbidities, operative details, and early ICU management are summarized in Table 1. In univariate analysis, low pre-operative ejection fraction, combined valve and coronary revascularization surgery, duration of CPB and higher APACHE III score on ICU admission were all associated with increased risk of post-operative AKI.

The relationships between baseline, post-operative, and 24 hr post-operative serum and absolute urine hepcidin (uHep), urinary hepcidin (uHep/uCr), and fractional excretion of hepcidin (FE Hepcidin) are shown in Table 2. At baseline, both urinary hepcidin and serum hepcidin were well within the normal ranges previously established for adults (Ganz et al. 2008, Blood 112: 4292-97). Urinary hepcidin was correlated with serum hepcidin in these patients at baseline ($r^2$=0.38, p<0.0001), but to a lesser degree than in younger, healthy adults. FE Hepcidin was calculated to be 8% in these patients at baseline which is higher than shown previously in younger adults (5%) using the same C-ELISA or time-of-flight mass spectrometry for hepcidin measurement (3%; Swinkels et al. 2008, PLoS One 2008; 3(7):e2706). There were no significant differences in uHep/uCr or serum hepcidin (sHep) between patients who received atorvastatin and those who received placebo and data from all patients were pooled for hepcidin analysis.

In all patients sHep, uHep, uHep/uCr and FE Hepcidin were all significantly elevated above baseline at both 6 and 24 hours (p<0.0001 for all comparisons with baseline). No significant relationship existed between AKI and 6 hour post-operative uHep/uCr values. At 6 hours uHep/uCr levels were abnormally elevated ~7-10 fold from baseline in both AKI and AKI-free patient's (3254 ng/mg and 5770 ng/mg, respectively) compared with normal median for adults (502 ng/mg creatinine; Ganz et al. 2008, Blood 112: 4292-97). Median uHep/uCr in AKI-free patient's continued to trend higher and remained highly elevated although the change in uHep/uCr between 6 and 24 hours in AKI-free patient's was not significant (7935 ng/mg; p=0.97). In contrast, median uHep/uCr levels decreased slightly, though not significantly between 6 and 24 hours (3859 versus 3845 ng/mg; Table 2).

Figure 7:
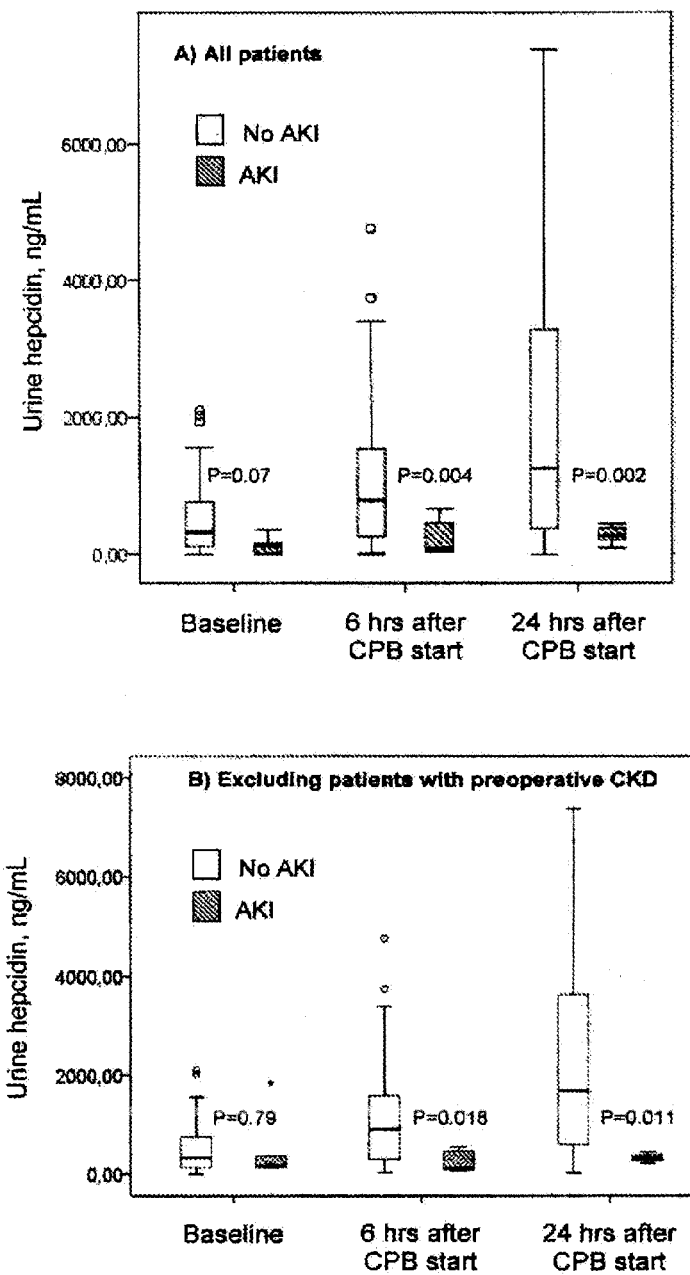
FIGS. 7A and 7B show urine hepcidin concentration over time in patients developing no acute kidney injury, AKI (white bars) compared to those with AKI (shaded bars). A) All patients, B) After excluding patients with chronic kidney disease, CKD.

Urine hepcidin (uHep), uHep/uCr, and FE Hepcidin were significantly lower at 24 hours in patients with AKI RIFLE≥R compared to AKI-free patients (Table 2). While the change in uHep/uCr between 6 and 24 hours within both AKI and AKI-free patient's groups was not significant, the increasing trend observed in AKI-free patient's paired with decreasing median uHep/uCr values for patient's developing AKI, led ultimately to highly significant differences at 24 hours between AKI and AKI-free patient's (Tables 2, 4, and 5 and FIGS. 1, 2, and 3). The decrease in uHep/uCr was greater and interestingly, the variability was lower around the median in patient classified with increasingly severe AKI, from RIFLE Risk to Injury to Failure (FIGS. 2, 7)

Serum hepcidin (sHep) did rise significantly between 6 and 24 hours in AKI-free patient's, to the high normal range of sHep in adults we have previously established (133 versus 242 ng/ml, respectively; p<0.0001) while in contrast no change is sHep was observed over the same time period although it also trended higher to levels that are just above the normal range for adults from the 6 hour median levels (Table 2).

Figure 2:
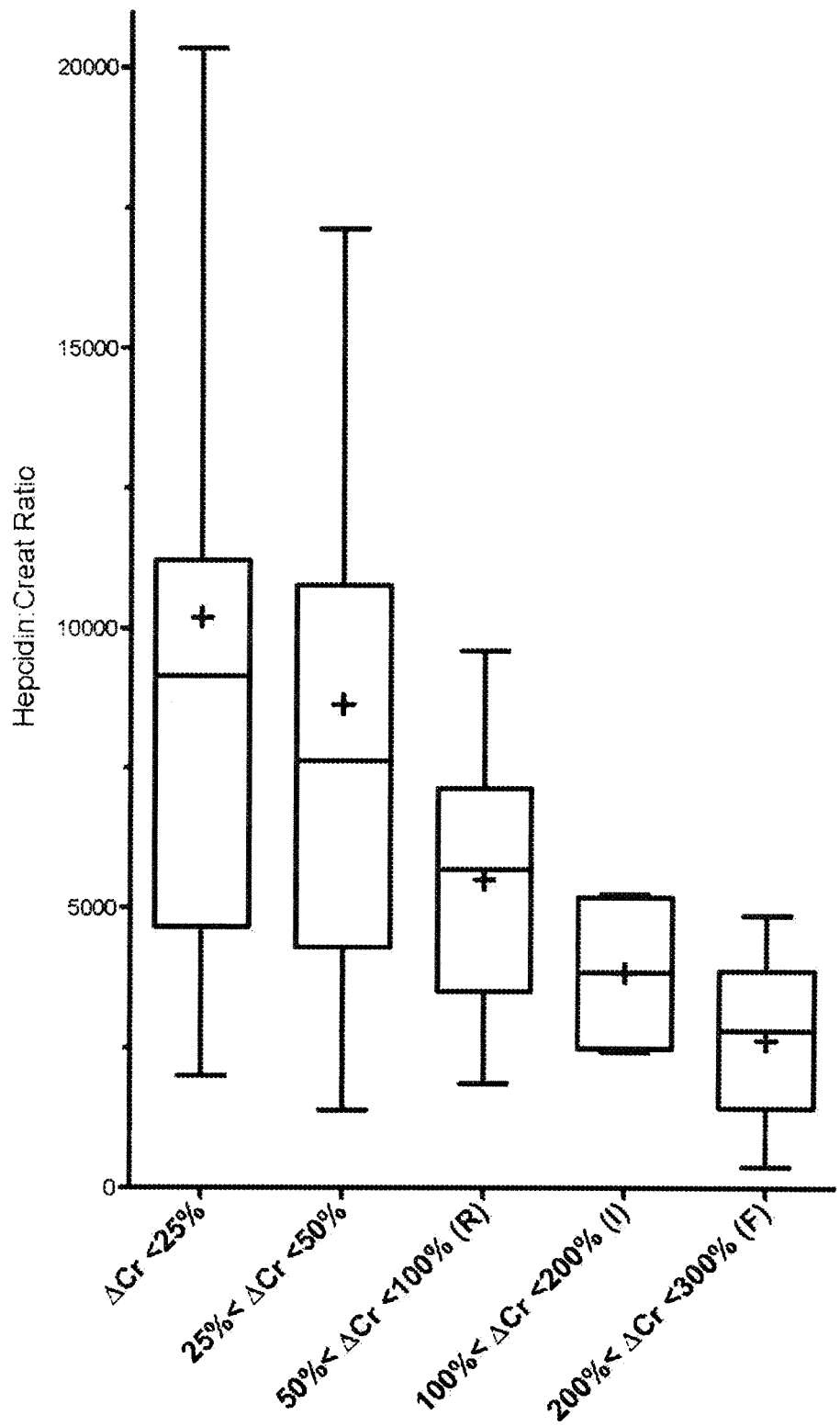
FIG. 2 shows urine hepcidin:creatinine at 24 hours and maximal AKI category after CPB.

FIG. 1 shows a post-operative changes in median uHep/uCr for patients with and without RIFLE R AKI. FIG. 1a demonstrates greater uHep/uCr levels at 24 hours in AKI-free patients compared to those with RIFLE≥R AKI. This separation was more marked when comparing more severe AKI (RIFLE I or F) to RIFLE R or no AKI (FIG. 1b). When examining increasing severity of AKI, lower mean and median uHep/uCr values were observed with more severe AKI when patients were categorized by their peak RIFLE class (FIG. 2).

Figure 3:
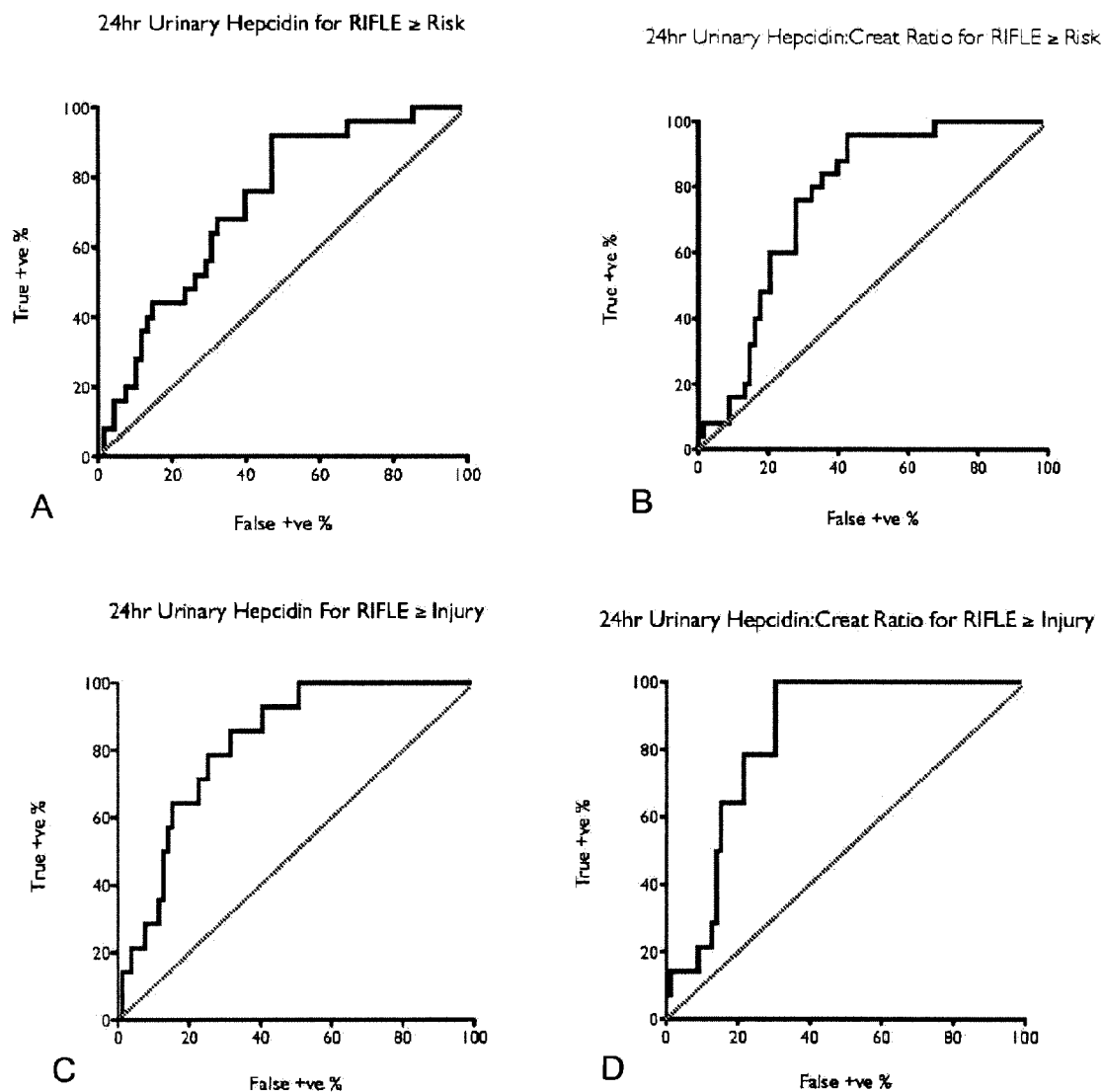
FIGS. 3A, 3B, 3C and 3D show ROC analysis for urinary hepcidin and urinary hepcidin:creatinine ratio for risk and injury.

ROC analysis demonstrated that lower uHep and uHep/uCr were sensitive and specific predictors of AKI with better performance at predicting more severe renal dysfunction and increasingly lower optimum cut-off point for diagnosis with more severe renal injury (Tables 3, 4, 5; FIG. 3). In this analysis, a 24-hour uHep/uCr of <5247 ng/mg had a 100% sensitivity and 70% specificity for diagnosis of RIFLE I AKI or greater post-operative AKI. Total area under the curve (AUC) of uHep/uCR at 24 hours for diagnosis of RIFLE≥I in the first five days after surgery was 0.84 (Table 4).

Association between urinary creatinine (uCr) and AKI needs to be placed in the context of changes observed in serum creatinine (sCr). The later increases slowly, and is only significantly elevated in some AKI patients 3 days post-operatively. When 16 of 25 patients who achieved RIFLE-R based on changes in sCr within 24 hours of surgery were excluded, uHep/uCr at 24 hours remained strongly predictive of severity of AKI in the 9 remaining AKI patients with remarkably similar cut-off values (Table 5).

Figure 4:
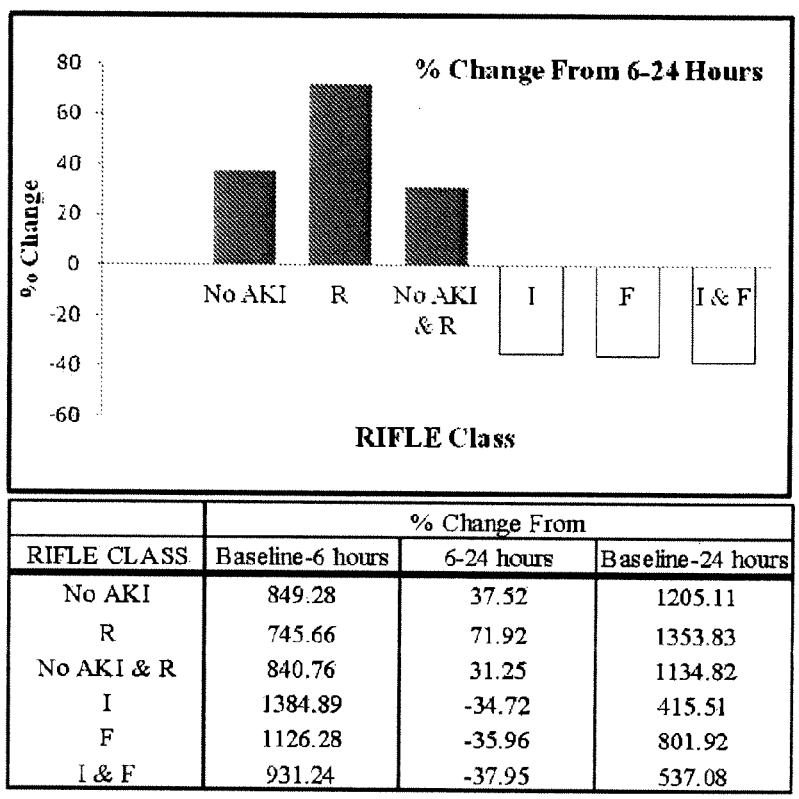
FIG. 4 shows a histogram of percent (%) change in uHep/uCr between 6 hr and 24 hr versus RIFLE classifications of increasing risk.

Table 6 shows median data for each group of RIFLE classification and FIG. 4 shows a histogram of percent (%) change in uHep/uCr between 6 hr and 24 hr versus RIFLE classifications of increasing risk. A significant negative percent (%) change is observed with increasing severity of AKI. Of key importance to certain aspects and embodiments of the instant disclosure, the AKI-free and RIFLE R groups exhibit a positive percent (%) change in uHep/uCr, whereas the RIFLE I and RIFLE F patients had a clearly negative percent (%) change between 6 and 24 hours (FIG. 4). In addition, the percent (%) changes between baseline and 24 hours after initiation of CPB surgery were significantly greater in the no AKI, RIFLE R, and no AKI plus RIFLE R groups, than the RIFLE I, RIFLE F, and RIFLE I plus RIFLE F groups (FIG. 4; see data table)

Table 7 shows ROC AUC analysis of various biomarkers that were also measured in serum and urine in the 93 patients from the CREAT trial and their ratios to uCr for discrimination of AKI by RIFLE criteria of AKI Risk (R), Injury (I), or Failure (F). The biomarkers we measured included urinary neutrophil gelatinase-associated lipocalin (uNGAL), serum NGAL (sNGAL), urine liver-type fatty acid binding protein (uL-FABP), urinary glutathione S-transferases (u-αGST; u-ΠGST), and urinary cystatin-C (uCy-c), prior to surgery (0 hr), 6 hours after beginning CPB-assisted surgery (6 hr), and 24 hours after CPB-assisted surgery.

Figure 5:
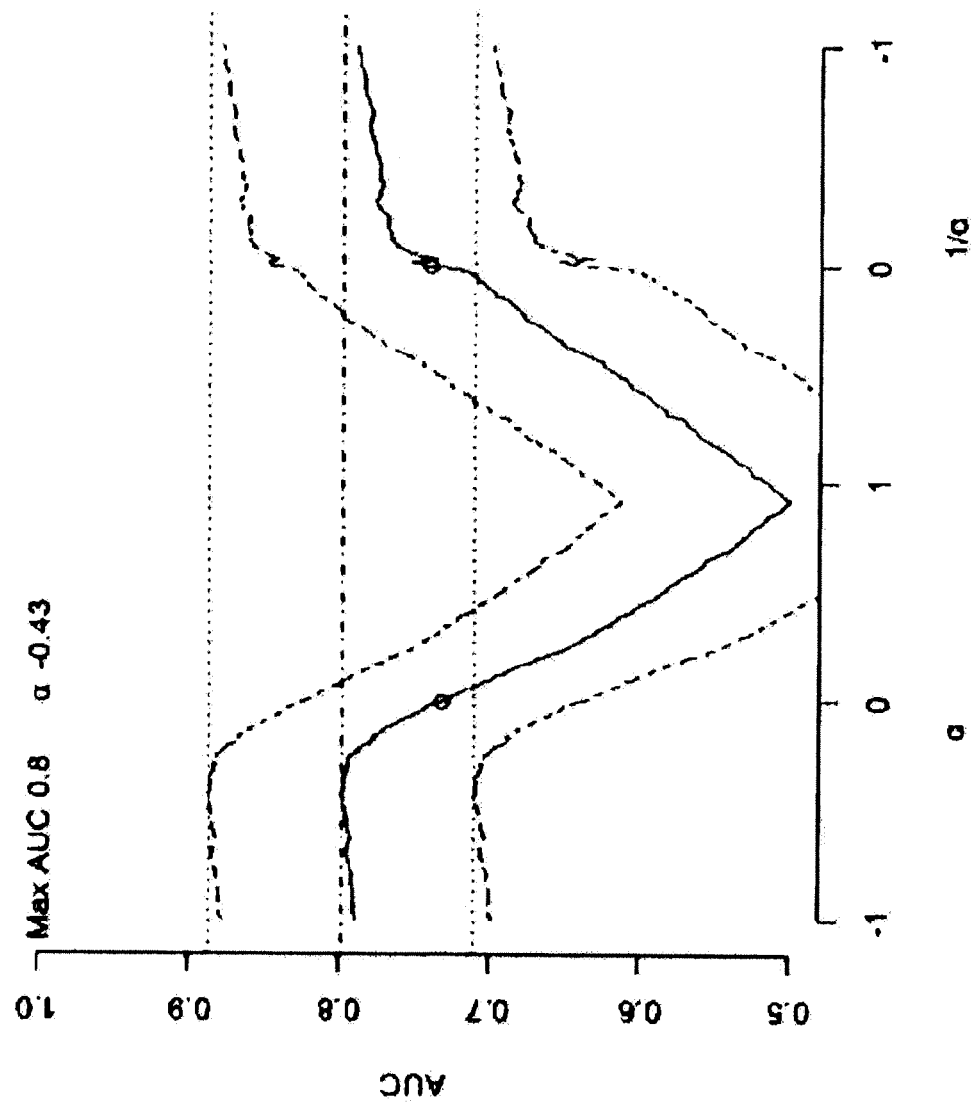
FIG. 5 shows weighted linear combination of change in urinary hepcidin creatinine ratio (uHep/uCr) at 24 hours and change in the urinary NGAL:creatinine ratio (uNGAL/uCr) at six hours for prediction of RIFLE R or greater class AKI in the five days after cardiac surgery.
Figure 6:
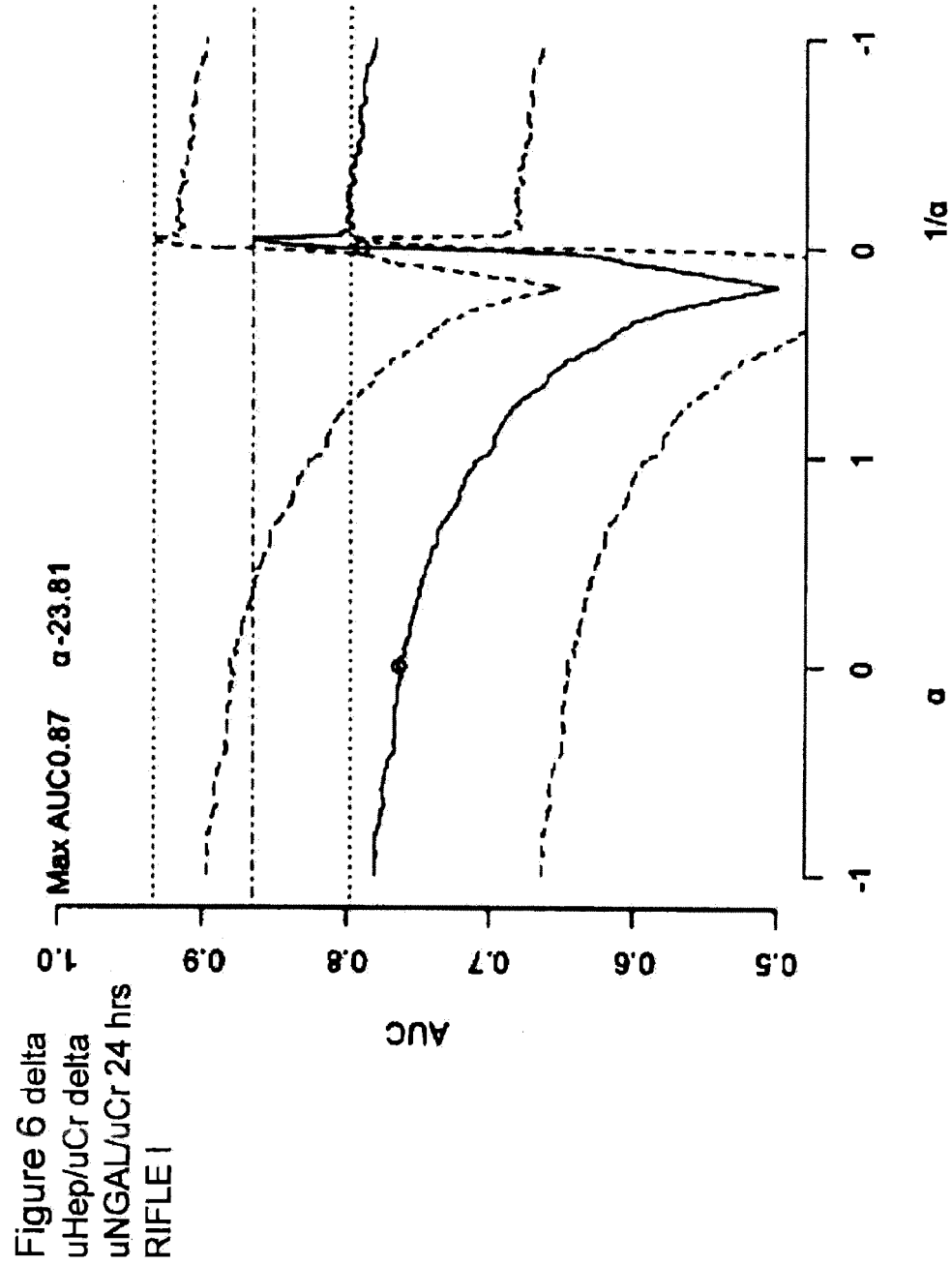
FIG. 6 shows weighted linear combination of the change in urinary hepcidin:creatinine ratio (uHep/uCr) expressed in ng/mg creatinine at 24 hours and change in urinary NGAL creatinine ratio (uNGAL/uCr) at 24 hours for prediction of RIFLE I or greater class AKI in the five days after cardiac surgery.

Linear combinations of two diagnostic test results can be analysed with the purpose of obtaining a maximal AUC for the combined score (Pepe, M. S. & Thompson, M. L., 2000, *Biostatistics* 1: 123-40). In this study, we also applied this method to the combination of uHep/uCr at 24 hrs and the ratio of urinary neutrophil gelatinase-associated lipocalin to urine creatinine (uNGAL/uCr) at 6 or 24 hours post-surgery for the prediction of increasing severity of AKI using the RIFLE consensus classification over the 5 days following surgery. Examples of these combinations are seen in FIGS. 5 and 6. FIGS. 5 and 6 shows a linear combination of uHep/uCr and uNGAL/uCr measurements at the indicated sample times for 2000 equally spaced values of α from −1 to +1 and 2000 equally spaced values of 1/α from −1 to +1 (equivalent to α−∞ to −1 and +1 to +∞). AUC (solid line) and a 90% confidence interval are plotted for each value of α, a 90% confidence interval is appropriate for a one-tailed comparison with individual markers because the best combination cannot be worse than the best of the individual markers. Circles show AUCs of individual markers and the dot-dashed lines show the AUCs of the optimal combinations. Statistical analysis was carried out and figures prepared in R: A language and environment for statistical computing. R Development Core Team (2009). R Foundation for Statistical Computing, Vienna, Austria. ISBN 3-900051-07-0, using material from the library Hmisc by Frank M Harrel Jr.

Based on the results outlined above, we elected to explore the utility of uHep/uCr and sHep in diagnosing AKI further in patients from a second registered clinical trial. To this end, we investigated 100 adult patients enrolled in the control arm of the BIC-MC study (Clinicaltrials.gov NCT00672334). This was a multicenter randomized controlled trial of perioperative sodium bicarbonate versus placebo for the prevention of AKI and an exploration of renal biomarkers in patients at increased renal risk undergoing cardiac surgery necessitating the use of CPB. Increased risk of AKI was defined as ≥1 risk factor for postoperative AKI: age ≥70 years; New York Heart Association class III/IV or left ventricular ejection fraction <35%; insulin-dependent diabetes mellitus; prior cardiac surgery; valvular surgery (with or without coronary artery bypass graft) or pre-operative serum creatinine >120 μmol/L. Exclusion criteria included patients undergoing emergency operation (≤24 hours from admission to hospital), off-pump surgery, patients presenting with advanced chronic kidney disease (serum creatinine >300 μmol/L) or kidney transplant and patients <18 years. Chronic kidney disease (CKD) was defined as preoperative estimated glomerular filtration rate <60 mL/min/1.73 m². Glomerular filtration rate was estimated using the Modification of Diet in Renal Disease Study equation re-expressed for use with the serum creatinine values standardized to isotope dilution mass spectroscopy. Renal replacement therapy (RRT) was initiated if the patient fulfilled at least one of the following clinical criteria: oliguria (urine output <100 mL/>6 hrs) that was unresponsive to fluid resuscitation measures, hyperkalemia (K>6.5 mmol/L), severe acidosis (pH<7.2) or clinically significant organ edema (e.g., lung) in the setting of renal failure.

As noted earlier, samples were obtained from 100 patients enrolled in the Placebo group (sodium chloride, 1.2 L starting with anesthesia induction and finishing 24 hours thereafter). Patients were recruited between January 2009 and June 2010. The local Institutional Review Board approved this investigation and written informed consent was obtained from each patient including the investigation of novel renal biomarkers. The study was carried out in compliance with the Helsinki Declaration.

Samples of plasma and urine were obtained simultaneously immediately after insertion of an arterial line ('baseline') before induction of anesthesia, at exactly 6 hours after commencement of CPB, and at exactly 24 hours after commencement of CPB. Timing of sampling was chosen to detect changes in uHep/uCR and other renal biomarkers before serum creatinine (sCr) increases would routinely occur in patients going on to develop AKI and was therefore limited to the first 24 hours after initiation of surgery. Aliquots of plasma and urine were frozen stored at −80° C. immediately after collection and centrifugation, and kept frozen on dry ice during transport.

Demographic and clinical data (Table 8) were collected at baseline and for the first 48 hours. Plasma creatinine (pCr) was measured at baseline, at 6 hours and 24 hours after commencement of CPB and daily within the first post-operative week and, if required, until hospital discharge. The primary outcome, AKI, was defined based on the baseline-to-peak pCr increase or urine output decrease during the first seven post-operative days using the RIFLE consensus definition of AKI. Additional analyses were performed to assess the ability of hepcidin to predict each RIFLE class and the need for RRT initiation.

Absolute urine hepcidin (uHep) values are expressed as ng/mL. To compensate for perioperative variation in urine dilution, uHep/uCr was calculated and expressed as ng hepcidin per mg creatinine (ng/mg). The sCr assays were carried out using the modified Jaffe method. (FE) Hepcidin was determined using the same formula described above.

Statistical analysis for this clinical study was performed using SPSS 16.0 (SPSS Inc, Chicago, Ill.) and MedCalc 11.5 (Mariakerke, Belgium). Categorical data were reported as percentages with 95% confidence interval of the mean percentage, and compared using Fisher's exact test. After testing for normal distribution, continuous data were reported as median with $25^{th}$-$75^{th}$ percentiles and non-parametric data was compared using the Mann-Whitney U test; continuous data over time were compared using the one-way repeated measures analysis of variance by ranks (Friedman test). We used nonparametric bivariate correlation and reported Spearman correlation coefficients (r). The ability of hepcidin to predict AKI was assessed by plotting receiver-operator characteristic (ROC) curves and further reported as areas under the curves (AUC) with 95% confidence intervals. An AUC-ROC value of >0.7 was taken to indicate a reasonable and >0.8 a good biomarker performance. AUC-ROC differences >0.1 units were defined as significant. ROC curve optimal cut-off values for AKI diagnosis, for curves with a statistically significant AUC, were defined as the point that maximized the Youden index, defined as (sensitivity+specificity)−1 (Youden W J, *Cancer* 1950, 3:32-35).

Univariate and multivariate stepwise regression analysis was undertaken to assess predictors of no AKI after CPB. Variables tested on univariate relation with incidence of no AKI included clinically relevant variables all displayed in Table 8, type and duration of surgery and renal biomarkers at 6 hours after start of CPB. Multivariate logistic regression modelling included clinically relevant variables with univariate P value <0.1 (age, atrial fibrillation, left ventricular ejection fraction [LVEF]<35%, chronic obstructive pulmonary disease [COPD], peripheral vascular disease [PVD]) and renal biomarkers. Logarithmic transformations were applied when necessary before multivariable logistic regression analyses were performed. Statistical significance was denoted by two sided P values of <0.05.

Overall, 394 consecutive patients were screened for the BIC-MC study. Two hundred patients were randomized, and all underwent CPB-assisted surgery. Of the 100 control patients analyzed for hepcidin, all had full clinical datasets and complete sampling except in two patients (no AKI) where plasma and urine samples at 24 hours after CPB could not be collected.

AKI-free patients (N=91) were younger and had less frequent preoperative atrial fibrillation and chronic obstructive pulmonary disease (Table 8). The type and duration of the operation did not differ between patients with postoperative AKI and those without, whereas perioperative fluid balance, dose of frusemide and volume of red blood cell transfusion were lower and outcome was better including less frequent need for RRT initiation in AKI-free patients (Table 9).

Figure 9:
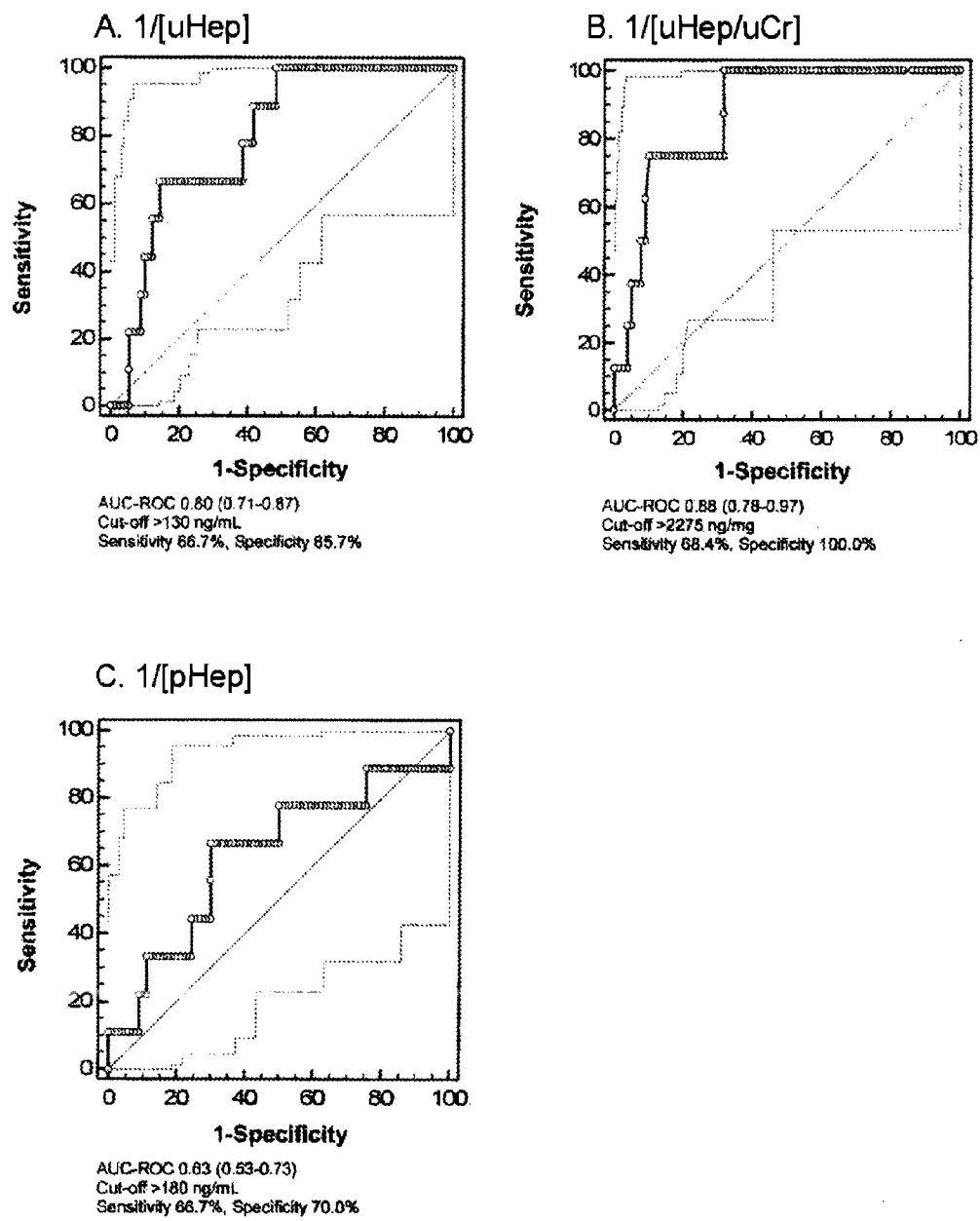
FIGS. 9A, 9B and 9C show predictive indices of hepcidin at 6 hours after commencement of cardiopulmonary bypass, CPB for NOT developing acute kidney injury (AKI). A) Urine hepcidin, B) Urine hepcidin/urine creatinine, C) Plasma hepcidin.

Starting with a non-significant difference at baseline, absolute urine hepcidin (uHep) levels were significantly higher in AKI-free patients at 6 hours and at 24 hours after commencement of CPB, (FIG. 7A). The AUC-ROC for uHep at 6 hours for the discrimination of AKI-free patients was 0.80 (FIG. 9A) and 0.81 for the prediction of RRT initiation (FIG. 10A). The predictive value at 24 hours remained essentially unchanged (no AKI: AUC-ROC 0.81, 95% CI 0.73-0.90; no RRT: 0.77, 95% CI 0.64-0.89).

When RIFLE class was considered, the AUC-ROC for uHep at 6 hours was 0.81 (95% CI 0.71-0.88; sensitivity 75%; specificity 86%) for not developing RIFLE R (R: N=4); 0.81 (95% CI 0.72-0.89; sensitivity 100%; specificity 62%) for not developing RIFLE I (I: N=3); and 0.75 (95% CI 0.65-0.83; sensitivity 100%; specificity 58%, cut-off >550 ng/mL) for not developing RIFLE F (F; N=2).

At 6 and 24 hours after commencement of CPB in the MIC-BC, uHep/uCr was significantly higher in patients not developing AKI (Table 10). At 6 hours after initiation of CPB surgery, the AUC-ROC was 0.88 for predicting an AKI-free status (FIG. 9B) and 0.88 for no RRT initiation (FIG. 10B). At 24 hours the AUC-ROC declined (no AKI: 0.68, 95% CI 0.50-0.87, no RRT: 0.73, 95% CI 0.53-0.92). Urine creatinine (uCr) at 6 hours after CPB alone did not separate patients with subsequent AKI from those without (Table 10).

In AKI-free patients in the MIC-BC trial, a urinary hepcidin/plasma hepcidin ratio >1 was observed ([uHep/uCr]/pHep. This ratio increased from 2.6 to 6.9 over the first 24 hours after initiation of surgery (Table 10). On the other hand, patients developing AKI, presented with a urinary hepcidin/plasma hepcidin ratio of around 1.0, which remained stable over time (Table 10). Overall, the highest fractional hepcidin excretion (FE Hepcidin) was detected at 6 hours after commencement of CPB. Yet, the FE Hepcidin was about 3 times higher in those not developing AKI (Table 10).

To examine the influence of preoperative CKD in patients participating in the BIC-MC study, we excluded patients who met the criteria stated above for CKD. The findings at baseline and interventions and outcomes remained essentially unchanged after patients with preoperative CKD were excluded from analyses (Tables 8, 9). The magnitude of uHep/uCr and pHep concentrations and increase over time or the predictive values of hepcidin did not differ significantly between patients with or without CKD (Table 11). Also, of note, preoperative uHep/uCr and pHep levels or the [uHep/uCr]/pHep ratio did not correlate with preoperative eGFR (all r<0.2, all P>0.1). These data point to the robustness of these urinary and plasma hepcidin concentrations for prediction of the ensuing severity of post-surgical AKI in patients who are undergoing CPB-assisted surgery.

Figure 8:
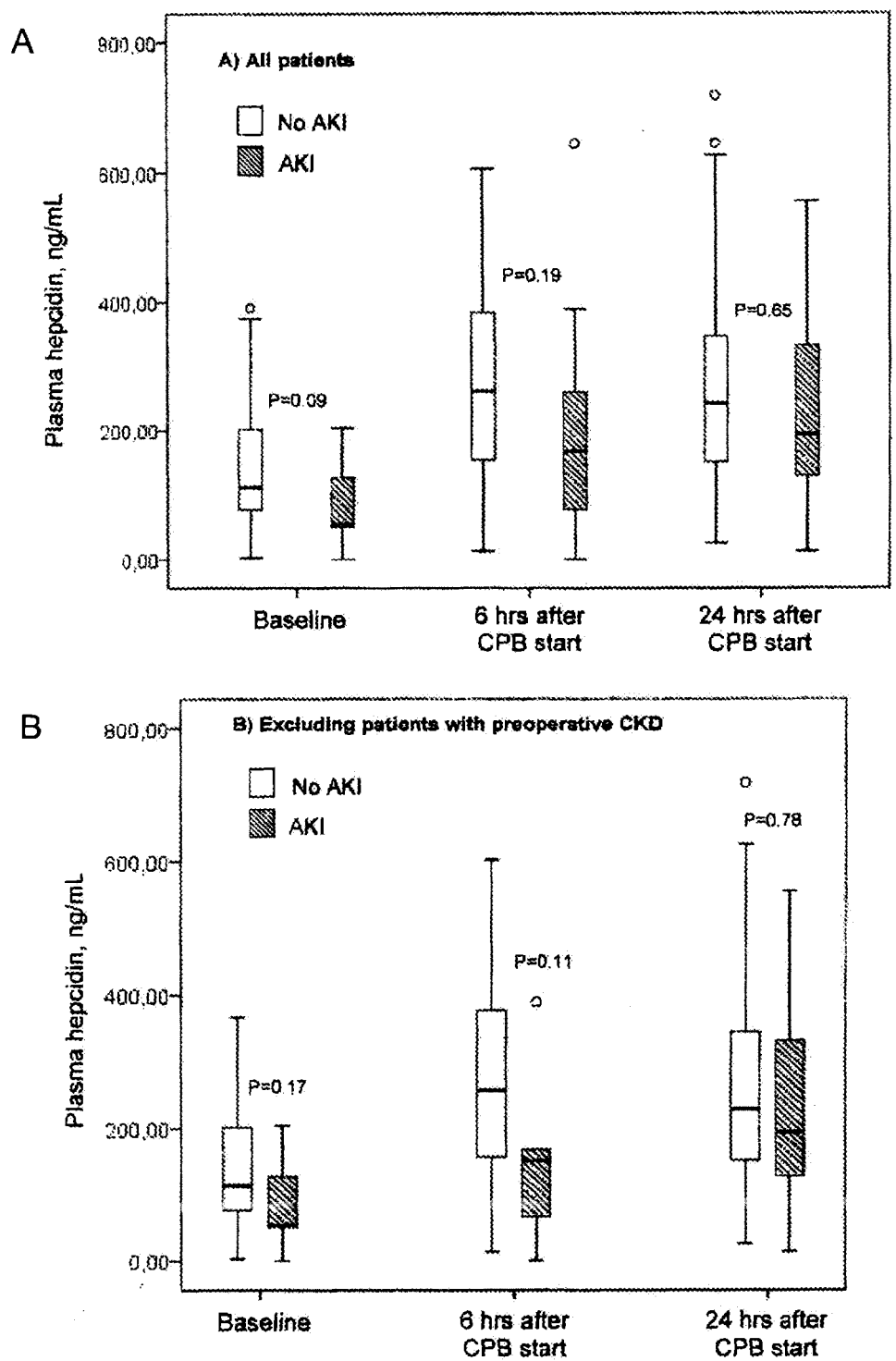
FIGS. 8A and 8B show plasma hepcidin concentration over time in patients developing no acute kidney injury, AKI (white bars) compared to those with AKI (shaded bars). A) All patients, B) After excluding patients with chronic kidney disease, CKD.

At baseline, patients who did not develop AKI had a pHep concentration of 112 (78-203) ng/mL, compared to 55 (50-146) ng/mL in patients who developed AKI (FIG. 8A). Hepcidin levels at 6 hours after the start of CPB tripled in patients who developed AKI (167 [73-325]) whereas they only doubled (261 [154-386]) in those who remained AKI-free. Post-operative plasma hepcidin concentrations had a lower AUC-ROC than urine hepcidin and was not useful in separating patients with or without AKI (FIG. 8A, 9C). The same applied to RRT initiation (FIG. 10C).

We further analyzed independent predictors of AKI. Six hours after commencement of CPB, uHep/uCr was the only independent predictive biomarker for "no AKI" (P=0.016; Table 12) and improved the quality of the model considerably (from $R^2$ 0.42 to $R^2$ 0.63). Serum creatinine at 6 hours after commencement of CPB had a limited AUC-ROC (0.69 [95% CI 0.48-0.93]) and was not an independent predictor (P>0.1) of AKI. Other clinical predictors (model 0) included age, impaired left ventricular ejection fraction, chronic obstructive pulmonary disease and peripheral vascular disease and were retained in models 1-3 after inclusion of renal biomarkers (Table 12).

We evaluated the correlation between uHep/uCr and plasma hepcidin (pHep) concentrations in the Placebo arm patients and found that at baseline, urine hepcidin adjusted for urine creatinine correlated well with plasma hepcidin (r=0.76, P<0.001) as has been previously shown for normal adults (Ganz et al. 2008, Blood 112: 4292-97). Importantly for some aspects and embodiments of the instant disclosure, a good correlation between postoperative plasma hepcidin and uHep/uCr in patients not developing AKI (at 6 hours after CPB: r=0.62, P<0.001) was found, but no correlation in those with subsequent AKI (at 6 hours after CPB: r=0.18, P=0.64). This indicates that patients who develop RIFLE criteria AKI have a disruption in normal hepcidin secretion.

Based on clinical data from a total of 193 patients undergoing CPB-assisted surgery enrolled in two registered clinical trials (CREAT, 93 patients; Clinicaltrials.Gov Nct00910221; BIC-MC, 100 patients; Clinicaltrials.gov NCT00672334) from 93, it was determined that the more elevated the uHep/uCr ratio at 24 hours following initiation of CPB, the lower the risk for development of AKI determined by RIFLE criteria in the ensuing four to five days.

In these clinical studies, the measurement of hepcidin involved use of a sensitive, quantitative competitive ELISA (C-ELISA) for hepcidin, which has been developed and used to establish the normal ranges of serum and urine hepcidin of adult men and women. The assay is described in published U.S. application 2009/0215095 (see Ganz et al., 2008, Blood 112: 4292-97). This assay has been validated in a number of disease states and has shown good correlation between serum and urinary hepcidin levels. Further, the quantitative C-ELISA does not suffer from any of the methodological weaknesses and ion-current normalization issues of the SELDI-TOF assay discussed by Ho et al. and Laarkeers et al., supra, which include lack of normalization of the hepcidin samples for creatinine and protein and the fact that it has not been validated in the urine of either normal or AKI patients, where proteinuria can confound results in SELDI-TOF based urine hepcidin assays significantly. The C-ELISA employs polyclonal antibodies that are highly specific to epitope(s) on human hepcidin-25 and does not require any sample preparation or technical instrument normalization for precise quantification of hepcidin in human serum, plasma, or urine. The C-ELISA also detects the hepcidin-22 and hepcidin-20 isomer (SEQ ID #2; SEQ ID #3), but to a lesser degree than hepcidin-25. The relative importance of the two N-terminally truncated isomers and their biological role in human physiology is currently unknown. Moreover, the hepcidin data generated in these clinical samples are expressed as ratios to urinary creatinine (ng hepcidin/mg creatinine), which may be expected to capture different elements of the disease process associated with CPB-mediated AKI. Additionally, these clinical studies used RIFLE criteria to differentiate patient's outcomes and related uHep/uCr into four potential outcomes of increasing severity of AKI: no AKI, Risk, Injury, and Failure, whereas the study of Ho et al. compared patients in only two groups, "no AKI" or Failure, in their observational study.

In addition to the above-described ELISA techniques, measurement of hepcidin in the present invention may be effected any of the many techniques and technologies for measuring hepcidin, e.g., quantitative hepcidin immunoassays (sandwich, solution, semi-quantitative and quantitative lateral flow devices) and mass spectrometry-based assays, such as HPLC-MS/MS, MALDI-TOF, SELDI-TOF, LC-electrospray triple-quadrupole MS/MS, and MRM.

Tables 2-6, 10, and 11 and FIGS. 1a and b, below, present or depict the uHep/uCr for no AKI and each of the RIFLE criteria that the inventors examined, RIFLE Risk (R), Injury (I), Failure (F); FIG. 1a, b), as well as a comparison of the grouping of no AKI, R, I, and F (FIG. 2). The data are shown for pre-CPB surgery (0 hrs), and 6 hrs and 24 hrs after initiation of CPB, respectively.

The baseline data show that the median values for uHep/uCr, sHep, or pHep for all the patients in both the CREAT and MIC-BC clinical study fell within the normal range in adults (urinary hepcidin, 71-1762 ng/mg Cr; serum or plasma hepcidin 17-245 ng/ml), as determined previously using the C-ELISA described above (Ganz et al. 2008). However, uHep/uCr values in each of AKI groups and the no AKI group of patients increased (~5-13 fold) beyond their median values for uHep/uCr at 6 hrs, although no individual RIFLE group differed significantly from another at that time point (Table 2, FIG. 1).

While no significant differences between individual RIFLE groups were observed at 6 hours in the CREAT study, we did observe significant differences in uHep/uCr at 6 hours in the BIC-MC study between patient's that developed AKI and AKI-free patient's (no AKI; Table 10; FIG. 7a). This significant difference remained after patient's with pre-operative CKD were removed from the dataset (FIG. 7b).

The difference in our observations at 6 hours in uHep/uCr is likely due to differences in surgical protocols, equipment, and possibly most significantly sample timing between the CREAT and BIC-MC studies. As shown above the first post-surgical samples were taken over a more prolonged period in the CREAT studies (3.58-9.13 hr; x=4.50 hr), whereas sampling was closely controlled in BIC-MC study and samples were taken at exactly 6 and 24 hours. The initiation of the physiological insult in CPB assisted surgery is defined and the hepatic response to elevated levels of the inflammatory cytokine, IL-B, and increased plasma iron-loading from mechanical damage to erythrocytes, prolonged. Since hepcidin is regulated by both IL-6 and plasma iron, it is reasonable to assume that liver production, serum concentrations, and urinary hepcidin excretion and measured levels (uHep/uCr) would continue to increase accordingly. Hepcidin levels in both serum and urine increase rapidly after oral iron is administered to a normal patient and peak approximately 12 hours after ingestion of an oral iron dose, and then return to normal at approximately 24 hours (Ganz et al. 2008).

At 24 hours post-surgery, median values for uHep/uCr in the no AKI and R group are shown to have increased well beyond their median levels at 6 hours, while conversely, in the I and F groups we observed flat or decreasing in uHep/uCr from their median levels at 6 hrs in both the CREAT and BIC-MC studies (Table 2; FIGS. 2, 4, 7). The clear difference in uHep/uCr between AKI-free and lower risk AKI patient's (RIFLE R) and AKI patients with more severe RIFLE classifications (RIFLE I & F) is shown in FIG. 4, where percent (%) change in uHep/uCr between 6 and 24 hours are plotted as a histogram. Patients with no AKI and/or RIFLE R AKI, post-surgically have positive percent (%) change in uHep/uCr, while those with RIFLE I and/or RIFLE F have negative percent (%) changes over this same time period. This relationship demonstrates that the greater the percent (%) change in uHep/uCr between 6 hrs and 24 hrs, the less severe the CPB-mediated AKI will be; conversely, that the lower or more negative the percent (%) change, the greater the severity of AKI post-surgically.

CPB is known to result in mechanical and shear force damage to red cells, causing the appearance of free hemoglobin, elevated levels of transferrin-bound iron, heme iron, and non-transferrin bound iron (NTBI) in the plasma after surgery, and in the induction of the inflammatory cytokine, IL-6. Elevated iron levels and/or IL-6 could be responsible for the persistent increase in uHep/uCr at 24 hours in patients classified with no AKI or RIFLE R AKI. In normal, healthy subjects, hepcidin returns to normal levels within 24 hours of ingesting an iron rich meals or iron supplement. In such people, iron is sequestered in macrophages (which recycle damaged erythrocytes) after ferroportin is down-regulated by hepatic hepcidin and iron transport activity into the plasma is reduced.

The observed decrease in uHep/uCr at 24 hours in the high risk RIFLE I and F groups was not predicted. This discovery reflects a key aspect of certain embodiments of the present invention. The decrease may reflect deterioration in renal removal of hepcidin in the face of ongoing synthesis of the hormone.

In some embodiments of the inventive methodology, uHep/uCr is established by assessing the values of uHep/uCr at an early time point and a later time point where a sample was obtained the value determined. A comparison of the values to determine if they are increasing or decreasing between the early and later time point may be used to establish the potential for the patient to experience no AKI, or enter the Risk classification, or enter the Injury classification, or enter the Failure classification. An example of this is shown in FIG. 1.

More specifically, FIG. 1 shows the median values for uHep/uCr prior to CPB-assisted surgery, at 6 hours and at 24 hours, of the AKI-free CPB patients vs. patients classified as either RIFLE R, I, and F. FIG. 2 shows the median values for uHep/Cr prior to CPB-assisted surgery, at 6 hours and at 24 hours, of the CPB patient's with no AKI and RIFLE R vs. patients with RIFLE I and RIFLE F.

This example demonstrates that those patients with no AKI have the largest increase in uHep/uCr from the 6 hour measurement (early timepoint) to the 24 hour measurement (late timepoint). The RIFLE R patients had increasing uHep/uCr between the 6 hour and 24 hour timepoints, but to lower levels than the no AKI patients. Conversely, those patients developing RIFLE I and RIFLE F AKI had decreasing levels of uHep/uCr between the 6 hour and 24 hour measurements, with those classified as RIFLE F, experiencing the largest decrease between the early and late uHep/uCr determinations.

Thus, results obtained via the inventive methodology, as described here, can inform a straightforward but important stratification of CPB surgery patient at a very early time after surgery, relative to current methods and biomarkers for AKI assessment, e.g., creatinine, GFR, and urine output. For instance, the CPB surgery patients may be grouped into the no AKI and RIFLE R group or the RIFLE I and F group, or low risk and high risk groups, respectively, by determining whether their uHep/uCr ratio was increasing or decreasing at 24 hours after CPB-assisted surgery, a great improvement over serum creatinine (sCr).

The present invention also provides methodology for early prediction of the severity of CPB-mediated AKI, using RIFLE criteria, where the value of uHep/uCr is measured before initiation of surgery (0 hours), at between about 3-12 hours initiation of surgery (such as CABG surgery) and the second sample is taken between about 6-24 hours; or about 24 hours after initiation of surgery. As part of this method, the percent (%) change of uHep/uCr between an early time point and a later time point is calculated and the determination of no AKI in patient following CPB surgery is made by a percent (%) change >35% in the value, while patients at risk (RIFLE R) of AKI are determined by a percent (%) change in uHep/uCr of >0% and <35% from the early to late time points. Conversely, patients who will likely development RIFLE I (Injury) AKI RIFLE F (failure) AKI, are determined by a decrease of 0 to about −35 percent (%) or greater. An example of this is shown in Table 2 and FIG. 4.

This description also contemplates early prediction of the severity of CPB-mediated AKI using RIFLE criteria, the baseline (0 hours) value of uHep/uCr is measured before initiation of surgery such as CABG surgery, at between about 3-12 hours and between about 6-24 hours; or about 24 hours after initiation of surgery In keeping with some aspects and embodiments of the inventive methodology, the value of uHep/uCr at an early time point and a later time point is measured and freedom from AKI in patients following CPB surgery is determined by a positive percent (%) change in uHep/uCr from the early to late times, while patients at risk (RIFLE R) of AKI are determined by a positive percent (%) increase in uHep/uCr to about 4700 ng/mg from earlier to late time points. Conversely, patients who will likely develop RIFLE I (Injury) AKI are identified by a decrease in uHep/uCr from earlier to later time points to about 3900 ng/mg. CPB surgery patients who will develop RIFLE F (Failure) AKI are determined by a decrease of uHep/uCr to about 2100 ng/mg creatinine or lower. An illustration of this connection appears in Table 1 and in FIG. 1.

Figure 11:
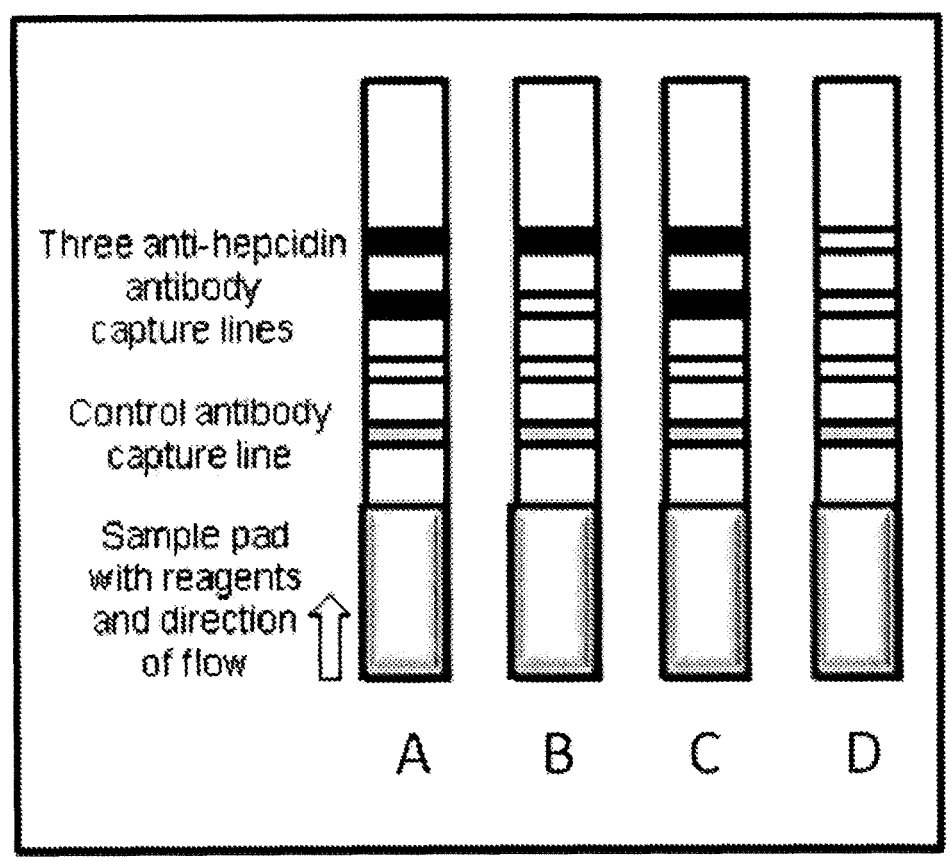
FIG. 11 shows an exemplary lateral flow device for rapid, semi-quantitative or quantitative assessment of urinary hepcidin following CPB-assisted surgery for RIFLE classification of AKI. The three upper hepcidin antibody capture lines and the lower capture line is a control IgG line to determine the device is functional. A. Pre CPB surgery. B. 6 hrs post initiation CPB for no AKI, R, I, and F. C. 24 hrs post initiation CPB for 1 and F. D. 24 hrs post surgery no AKI or R. Cutoffs for upper line >4500 ng/mg Cr, middle line >3000 ng/mg, lower line >1000 ng/mg Cr.

In accordance with certain embodiments of the invention, methods are provided in which urinary hepcidin, not corrected for creatinine and expressed simply as ng hepcidin per ml urine (uHep), is measured before initiation of surgery (0 hours), between about 3-12 hours, at about 3-9 hours; or about 4-8 hours; or about 5-7 hours; or about 6-12 after initiation of surgery (such as CABG surgery); further, another sample is taken between about 6-24 hours; or about 24 hours after initiation of surgery. As part of this method, lower uHep levels predicts higher risk AKI, including RIFLE I and RIFLE F and could be used to determine whether a patient is at high risk (RIFLE I and F) of AKI or at low risk group for AKI (no AKI and RIFLE R) following CPB-assisted surgery. Tables 2, 3, and 11 as well as FIGS. 10 and 11 illustrated the utility of uHep to differentiate patients into high risk groups with good discriminatory power.

As part of this specific method and other methods and embodiments of the present invention, receiver-operating characteristic (ROC) area under the curve (AUC) analysis can be applied to assess the utility of uHep for classifying CPB patients into correct RIFLE risk category. ROC AUC is most widely used index of diagnostic accuracy for diagnostic tests with continuous or ordinal data. An ROC curve shows the trade-offs between increasing true positive and increasing false positive rates that are feasible with a diagnostic score. The area under an ROC curve (AUC) is a summary measure of accuracy ranging from 0.5 (no discrimination) to 1 (perfect discrimination).

Examples of ROC AUC analysis from both the CREAT and MIC-BC demonstrating the discriminatory utility of uHep at 24 hours, and uHep/uCr at 24 hours, and the change in uHep/uCr from baseline at 24 hours (A uHep/uCr 24 hr) are presented in Tables 3, 4, 5, 11, and 12: FIGS. 3, 5, 6, 9, and 10. Examination of the AUC for each of these hepcidin measurements shows good agreement between the two studies, which were conducted at different international sites. In the CREAT trial, the ROC AUC for uHep at 24 hours was 0.81, 0.85, and 0.83 (MIC-BC), respectively, which indicated good to very good discriminatory ability for RIFLE F AKI for each of these markers, and good discrimination for RIFLE I AKI for the same markers at 24 hours with ROC AUC of 0.82 (CREAT), 0.84 (CREAT), and 0.75 (MIC-BC).

With respect to distinguishing data from two diagnostic tests, in order to predict diseased and non-diseased state, the tests may measure the same aspect of a disease process and, while quite good individually, contribute little added information to prediction based on a similar biomarker (Table 7). Conversely, test examining different elements of a disease process may demonstrate greatly enhanced discriminatory ability in combination. Yet, individual tests vary in absolute magnitude and range of their diagnostic score and may vary in their predictive ability in differing clinical contexts and with differing outcome measures. Combinations of scores thus need to be appropriately weighted to obtain the optimally predictive combination. Linear combinations of two diagnostic test results can be analyzed with the purpose of obtaining a maximal AUC for the combined score (Pepe, M. S. & Thompson, M. L., 2000, *Biostatistics* 1: 123-40). These combinations take the form $S=Y1+\alpha Y2$ where S is the combine score and Y1 and Y2, the individual diagnostic tests. The coefficient $\alpha$ is varied from $-\infty$ to $+\infty$ such than $\alpha=0$ represents the effect of test Y1 alone and $\alpha=\pm\infty$ represent the effect of test Y2 alone with values of $\alpha$ in between these values representing different weighted linear combinations. AUCs for these combinations can be calculated empirically, plotted and an AUC at an optimal value of $\alpha$ evaluated (FIGS. 4, 5).

These same data demonstrated that, conversely, the higher the urinary NGAL to urinary creatinine ratio (uNGAL/uCr) at 24 hours following initiation of CPB, the higher the risk of developing CPB-mediated AKI determined by RIFLE criteria over the ensuing four to five days. Thus, the change in these ratios, both individually and weighted linear combinations or, in others cases, a ratio from 6 hours (entry into ICU following completion of CPB-assisted surgery) to 24 hours (post-initiation of CPB-assisted surgery), to be predictive of the severity of CPB-mediated AKI as determined by RIFLE criteria over the ensuing four or five days. Moreover, these data also support use of the change in uHep/uCr to sHep ([uHep/uCr]/sHep) between 6 and 24 hours, to predict the severity of CPB-mediated AKI over the ensuing four or five days (Table 10). It follows, too, that addition of serum NGAL/serum creatinine (sNGAL/sCr) or uNGAL/uCr, in weighted linear combinations or as ratios, will increase the sensitivity and specificity of the predictions based on this ratio (see FIGS. 5 and 6). When analyzing individual markers, larger rises in urinary NGAL are associated with AKI, while smaller rises in urinary hepcidin predict AKI. Thus, combinations of hepcidin minus NGAL (or vice-versa) may interact to enhance diagnostic accuracy. In many situations there was a trend for the optimal combination of markers to be better than each individual marker alone and this reached statistical significance in some cases (Table 7). This indicates that uHep/uCr and uNGAL are reflecting different aspects of the pathogenesis of AKI, and combination of markers may enhance diagnostic accuracy. In some embodiments, a combined score may be appropriately weighted to increase usefulness.

As indicated this weighting may vary in different contexts. The following process may be employed, from a cohort of patients sharing similar clinical context an optimal combination of biomarker scores would be established predicting a specific grade of kidney injury of clinical relevance in management as described above. This weighted combined score would then be validated as a superior predictor of outcome in a similar cohort of patients. A cut-off value giving best balance between false and true positive rates could then be established for this score using conventional ROC analysis. Following this the weighted combined score cut-off could be made available as a proprietary diagnostic algorithm for use in the patients with similar characteristics to the development groups. Several such algorithms may be developed to applying to different clinical context and outcomes and these may then be assessed according to the context or utilized in an expert system approach.

A further embodiment of the present disclosure is a lateral flow device for rapid, semi-quantitative or quantitative assessment of uHep/uCR following CPB-assisted surgery for RIFLE classification of AKI. An example is shown in FIG. 11. The three upper hepcidin antibody capture lines and the lower capture line is a control IgG line to determine the device is functional.

A further embodiment of this disclosure is a lateral flow device (LFD) for rapid, semi-quantitative or quantitative assessment of urinary hepcidin following CPB-assisted surgery for RIFLE classification of AKI. An example is shown in FIG. 11. The three upper hepcidin antibody capture lines and the lower capture line is a control IgG line to determine the device is functional. In an LFD according to some embodiments of the present disclosure, a high affinity antibody to hepcidin would be applied to a high protein binding strip of a material such as nitrocellulose with a non-absorbant support backing in distinct lines using standard methods. The concentration of the antibodies would be adjusted to predetermined concentrations, thereby to produce different levels of binding capacity across the three bands in a way that produces a "cut-off" value, allowing visual determination of the concentration in the urine sample applied to the device. Pursuant to this modified competitive ELISA diagnostic method, a known amount of labeled synthetic hepcidin competitor would be incorporated into the sample pad during manufacture. Pursuant to the disclosure, the competitor could in some embodiments be a synthetic hepcidin conjugated to colloidal gold, or biotin, a ligand, or an enzyme such as horseradish peroxidase, or a fluorescent reporter.

In keeping with some aspects and embodiments of the present disclosure, the known amount of competitor molecule will compete for antibody binding sites after a know volume or amount of urine adjusted for creatinine concentration of a patients urine is applied to the sample pad. An absorbent wick incorporated into the LFD then will cause flow of the urine sample and competitor solution upward on the LFD and across the anti-hepcidin capture lines and control capture line, respectively. After the solution has reached the top of the LFD, the result will read.

As described above, the inventors have demonstrated the possible outcomes of applying a sample from a patient who will develop RIFLE I or RIFLE F AKI (FIG. 11C) and one that will not (FIG. 11D). Samples from both patients would be expected to yield the result shown in FIG. 11B, where the cutoff is adjusted to about 3000 ng/mg creatinine hepcidin due to rise in uHep/uCr at 6 hours in a given CPB surgery patient. At 24 hours, however, the urine sample of a patient likely to develop RIFLE I or F AKI will have lower concentrations of urine hepcidin, which would cause the sample to fail to compete with antibodies on middle capture line due to the 4500 ng/mg creatinine cutoff (FIG. 6C). Conversely, higher levels of urinary hepcidin in no AKI patients would occupy all the binding sites in the middle and upper capture lines (cutoff >7300 ng hepcidin/mg creatinine) and yield the result seen in FIG. 6D. The lower line would be set to a cutoff in the normal range (1000 ng hepcidin/mg creatinine) and, in most cases of no AKI and RIFLE AKI, patients would be efficiently competed away (FIG. 6B), except possibly in the case where failure led to complete kidney failure in its filtering function. Thus, pursuant to the invention a device could be used to predict catastrophic kidney failure as well.

The various aspects and embodiments described here document the utility and potential of hepcidin measurements to provide rapid diagnosis of diseases, particularly acute kidney damage. The data can be expressed in a number of ways: absolute urine hepcidin (uHep) and urine hepcidin corrected for urine creatinine (uHep/Cr) as well as their ratios to serum (sHep) or plasma hepcidin (pHep), the fractional excretion rate of these uHep and uHep/uCr and their ratios. Absolute values, kinetics of change over defined time periods of 6 hours or less defined as percent (%) change, and mathematical derivatives are shown, in accordance with the invention, to possess utility for predicting kidney injury, as scored by RIFLE criteria.

The biological basis for many of the aspects and embodiments of the present invention is the secretion into the blood of hepcidin, predominantly by the liver, in response to changes in iron levels and inflammatory cytokines, especially IL-6. Iron and IL-6, both strong, positive regulators of liver hepcidin secretion, have been shown to be produced at significant levels upon initiation of CPB-assisted surgery, particularly in cardiac surgeries such as CABG, valve and tissue transplants, and organ transplants (heart, lung, liver, kidney).

Hepcidin is exquisitely sensitive to changes is plasma iron and in normal patients goes from baseline to peak levels in around 12 hours and then returns to baseline following a dose of 65 mg iron sulfate. This same pattern, although more sustained, is seen in acute inflammatory events. Inflammation associated with pre-CKD, CKD, and rheumatoid arthritis leads to chronic stimulation of hepcidin production by the liver. The hepcidin blocks iron absorption and recycling from senescent erythrocytes and causes anemia of inflammation (AI), also known as anemia of chronic disease (ACD).

The response of hepcidin to iron released from damaged red blood cells and IL-6 from damaged tissues following CPB surgery, the rapidity of the hepcidin response, the filtration of hepcidin by the kidney, and the excretion of hepcidin into the urine collectively underlie hepcidin's value as a biomarker for prediction of kidney injury, particularly AKI, following CPB and other forms of cardiac, metabolic, hemotologic, pathogenic, and inflammatory diseases.

In various aspects and embodiments of the present disclosure, urine and serum hepcidin measurements may be superior to the current gold standard, serum creatinine (sCr), because of hepcidin's rapid response to changes in plasma iron and IL-6. Whereas hepcidin is shown in these embodiments to change quickly and by many-fold within 5-6 hours, serum creatinine responds much more slowly. As many as 2-5 days are required to detect AKI by means of serum creatinine changes in some patients. As shown here, therefore, hepcidin can be at least an order of magnitude faster in producing a diagnostic indication of the potential severity of RIFLE classified AKI. In the some embodiments, methods and devices are provided that ca differentiate between the AKI-free condition alone or in combination of RIFLE R, and the more severe forms of RIFLE I and F AKI. Based on ROC AUC analyses, several examples of which are shown here, hepcidin levels and the various derivative measurements described here have good or very good diagnostic utility.

The rapid diagnosis and staging of AKI by means of hepcidin measurements, pursuant to the invention, may enable the development of novel therapeutic interventions and drugs for CPB-assisted surgeries, aortic aneurism repairs, and "off-pump" and minimally invasive cardiac and organ transplant surgeries. Heretofore, rapid diagnosis of impending kidney injury was not possible. In addition, hepcidin and related embodiments may allow improvements in existing equipment, therapeutic protocols and procedures, treatments, particularly renal replacement therapies (RRT) and kidney-sparing therapies and drugs. Urine and serum hepcidin are important biomarkers for kidney injury.

TABLE 1

| Variable | All | AKI (n = 25) | No AKI (n = 68) | p-value |
|---|---|---|---|---|
| Baseline Characteristics | | | | |
| Age (yrs) | 70 (61-76) | 72 (67-78) | 70 (61-75) | 0.14 |
| Female Sex | 31% (22-41) | 32% (12-52) | 30% (20-42) | 1.0 |
| Pre-operative Creatinine | 91 (76-113) | 86 (72-111) | 95 (78-119) | 0.29 |
| CKD 3 | 29% (20-38) | 24% (6-42) | 31% (20-42) | 0.61 |
| CKD 4 | 8% (2-13) | 16% (1-31) | 4% (0-9) | 0.08 |
| IDDM | 7% (2-13) | 8% (0-19) | 7% (1-13) | 1.0 |
| Previous CTS | 16% (9-24) | 20% (3-37) | 15% (6-23) | 0.53 |
| LVEF <35% | 6% (1-11) | 16% (0-32) | 3% (0-7) | 0.04* |
| Surgery | | | | |
| CABG | 59% (49-69) | 76% (58-94) | 53% (41-65) | 0.06 |
| Valve | 62% (52-72) | 68% (48-88) | 60% (48-72) | 0.63 |
| CABG + Valve | 25% (16-34) | 48% (27-69) | 16% (7-25) | 0.003* |
| Thoracic Aortic Surgery | 11% (4-17) | 20% (3-37) | 7% (1-13) | 0.13 |
| Duration of bypass (min) | 139 (11-202) | 210 (146-240) | 125 (106-177) | 0.0004* |
| Post-operative | | | | |
| APACHE III | 50 (41-57) | 52 (47-69) | 47 (40-56) | 0.0024* |
| % Blood transfusion in theatre or first 24 hours | 41% (31-51) | 56% (35-77) | 35% (24-47) | 0.096 |
| Any Vasopressor in ICU | 48% (37-58) | 58% (37-80) | 44% (32-56) | 0.35 |
| Any Inotrope in ICU | 41% (31-51) | 44% (23-65) | 40% (28-52) | 0.81 |
| Fluid balance (first 24 hours post-op) | +190 (−886 to +1366) | +43 (−640 to +726) | +310 (−103 to +723) | 0.73 |

TABLE 2

| Variable | All | AKI (n = 25) | No AKI (n = 68 I) | p-value |
|---|---|---|---|---|
| uHep, ng/ml | | | | |
| pre-op | 487 (162-993) | 495 (132-961) | 482 (172-1053) | 0.73 |
| post-op | 633 (214-1522) | 698 (236-1796) | 628 (214-1547) | 0.80 |
| 24 hours | 4951 (1792-13034) | 2881 (857-5577) | 8580 (2546-13964) | 0.0009 |
| sHep, ng/ml | | | | |
| pre-op | 80 (44-114) | 73 (42-146) | 81 (46-112) | 0.88 |
| post-op | 144 (90-215) | 176 (102-252) | 133 (84-206) | 0.06 |
| 24 hours | 239 (166-346) | 227 (125-337) | 242 (189-356) | 0.28 |
| uHep/uCr (ng/mg) | | | | |
| pre-op | 526 (289-1071) | 427 (286-984) | 608 (295-1139) | 0.31 |
| post-op | 5594 (2474-11034) | 3859 (2398-9971) | 5770 (2882-11053) | 0.37 |
| 24 hours | 6514 (3362-10211) | 3845 (2650-5243) | 7935 (4464-11092) | <0.0001 |
| FE Hepcidin | | | | |
| 0 hours | 8.6% (4.6-12.9) | 8.6% (3.6-10.3) | 8.6% (5.8-13.7) | 0.24 |
| post-op | 45.5% (24.5-74.5) | 41.3% (13.3-59.5) | 47.7% (26.3-78.0) | 0.092 |
| 24 hours | 36.0 (21.2-52.2) | 27.4% (14.2-41.8) | 37.1% (23.1-57.6) | 0.049 |
| sCr (µmol) | | | | |
| Baseline | 91 (75-113) | 86 (72-112) | 95 (77-119) | 0.29 |
| Post-op | 103 (81-118) | 109 (79-130) | 101 (81-112) | 0.20 |
| 24 hr | 113 (93-140) | 144 (120-166) | 107 (92-125) | 0.0003 |
| uCr (mmol) | | | | |
| Baseline | 7.3 (4-12.7) | 8.0 (3.7-14.4) | 6.6 (4.1-10.0) | 0.11 |
| Post-op | 1.5 (0.61-3.2) | 2.1 (0.60-3.6) | 1.3 (0.60-3.1) | 0.42 |
| 24 hr | 8.8 (5.0-13.0) | 5.9 (3.2-10.3) | 10.0 (5.8-13.2) | 0.048 |

TABLE 3

Urine Hepcidin (ng/ml)

| Time | Endpoint | AUC-ROC (95% CI) | Sensitivity % | Specificity % | Cut-off ng/ml | p-value |
|---|---|---|---|---|---|---|
| Pre-op | RIFLE R or worse vs. 0 | 0.52 (0.39-0.66) | NA | NA | NA | 0.73 |
| | RIFLE I or worse vs. R or 0 | 0.60 (0.45-0.75) | NA | NA | NA | 0.24 |
| | RIFLE F vs. I, R or 0 | 0.61 (0.44-0.78) | NA | NA | NA | 0.26 |
| Post-op | RIFLE R or worse vs. 0 | 0.52 (0.38-0.65) | NA | NA | NA | 0.79 |
| | RIFLE I or worse vs. R or 0 | 0.50 (0.34-0.67) | NA | NA | NA | 0.96 |
| | RIFLE F vs. I, R or 0 | 0.51 (0.31-0.71) | NA | NA | NA | 0.94 |
| 24 hours | RIFLE R or worse vs. 0 | 0.73 (0.62-0.83) | 92 | 53 | <7856 | 0.00088 |
| | RIFLE I or worse vs. R or 0 | 0.82 (0.73-0.92) | 93 | 59 | <4731 | 0.0001 |
| | RIFLE F vs. I, R or 0 | 0.81 (0.68-0.93) | 90 | 56.6 | <4731 | 0.0015 |

TABLE 4

Urine Hepcidin:Urine Creatinine (uHep/uCr)

| Time | Endpoint | AUC-ROC (95% CI) | Sensitivity % | Specificity % | Cut-off ng/ml | p-value |
|---|---|---|---|---|---|---|
| Pre-op | RIFLE R or worse vs. 0 | 0.57 (0.44-0.70) | NA | NA | NA | 0.31 |
| | RIFLE I or worse vs. R or 0 | 0.58 (0.44-0.73) | NA | NA | NA | 0.31 |
| | RIFLE F vs. I, R or 0 | 0.66 (0.50-0.82) | NA | NA | NA | 0.10 |
| Post-op | RIFLE R or worse vs. 0 | 0.56 (0.43-0.69) | NA | NA | NA | 0.36 |
| | RIFLE I or worse vs. R or 0 | 0.53 (0.37-0.69) | NA | NA | NA | 0.71 |
| | RIFLE F vs. I, R or 0 | 0.60 (0.43-0.77) | NA | NA | NA | 0.29 |
| 24 hours | RIFLE R or worse vs. 0 | 0.77 (0.67-0.86) | 96 | 57.35 | <7313 | <0.0001 |
| | RIFLE I or worse vs. R or 0 | 0.84 (0.75-0.92) | 100 | 69.6 | <5247 | <0.0001 |
| | RIFLE F vs. I, R or 0 | 0.85 (0.77-0.94) | 100 | 68.7 | <4992 | 0.0003 |

TABLE 5

Urine Hepcidin:Urine Creatinine (uHep/uCr)
Excluding patients with RIFLE-R[Cr] or greater within 24 hr.

| Time | Endpoint | AUC-ROC (95% CI) | Sensitivity % | Specificity % | Cut-off ng/ml | p-value |
|---|---|---|---|---|---|---|
| 24 hours | RIFLE R or worse vs. 0 | 0.78 (0.66-0.90) | 100 | 57.35 | <7313 | 0.006 |
| | RIFLE I or worse vs. R or 0 | 0.86 (0.75-0.97) | 100 | 73.2 | <5135 | 0.003 |
| | RIFLE F vs. I, R or 0 | 0.90 (0.78-0.99) | 100 | 73.6 | <4992 | 0.004 |

TABLE 6

Urinary hepcidin (uHep/uCr) expressed as ng/mg creatinine prior to initiation of CPB (0 hrs), 6 hrs, and 24 hrs grouped according to RIFLE criteria for CPB-mediated AKI, including Failure (F), Injury (I), Risk (R), and No AKI. Additional grouping include Injury and Failure (I + F) and Risk and No AKI (R + No AKI). The overall median values (Median) and quartile 1 (Q1) and quartile 3 (Q3) medians are shown. Also shown are the fold increases from 0 hr (baseline) at 6 hr and 24 hr, and the % change in uHep/uCr between 6 and 24 hours after initiation of CPB-assisted surgery.

| | RIFLE F | | | RIFLE I | | | RIFLE R | | |
|---|---|---|---|---|---|---|---|---|---|
| Hours | Median | Q1 | Q3 | Median | Q1 | Q3 | Median | Q1 | Q3 |
| 0 | 312 | 214 | 562 | 748 | 436 | 1309 | 392 | 286 | 1274 |
| 6 | 3826 | 990 | 8154 | 11107 | 3561 | 17022 | 3315 | 803 | 9971 |
| 24 | 2814 | 1433 | 3877 | 3856 | 2493 | 5188 | 5699 | 3518 | 7137 |
| Fold increase 0-6 hr | 12.1 | 2.5 | 27.5 | 12.9 | 7.1 | 16.4 | 4.8 | 2.2 | 14.0 |
| Fold increase 0-24 hr | 6.7 | 4.9 | 9.1 | 5.7 | 2.6 | 9.7 | 9.0 | 3.4 | 12.7 |
| Fold increase 6-24 hr | 0.6 | 0.3 | 1.0 | 0.5 | 0.2 | 1.0 | 1.0 | 0.6 | 5.3 |

| | No AKI | | | RIFLE I + RIFLE F | | | RIFLE R + No AKI | | |
|---|---|---|---|---|---|---|---|---|---|
| Hours | Median | Q1 | Q3 | Median | Q1 | Q3 | Median | Q1 | Q3 |
| 0 | 608 | 295 | 1139 | 445 | 233 | 863 | 606 | 292 | 1159 |
| 6 | 5770 | 2882 | 11053 | 4569 | 2113 | 12469 | 5701 | 2471 | 10997 |
| 24 | 7935 | 4464 | 11092 | 2835 | 2147 | 4220 | 7483 | 4407 | 10774 |
| Fold increase 0-6 hr | 9.2 | 4.4 | 20.6 | 8.3 | 4.2 | 17.6 | 12.9 | 5.0 | 19.4 |
| Fold increase 0-24 hr | 10.5 | 5.9 | 19.7 | 10.5 | 5.8 | 16.9 | 6.3 | 4.3 | 9.1 |
| Fold increase 6-24 hr | 1.4 | 0.5 | 2.9 | 1.4 | 0.6 | 3.0 | 0.6 | 0.3 | 1.0 |

TABLE 7

ROC AUC analysis of various biomarkers and their ratios to urinary creatinine (Cr) for discrimination of AKI by RIFLE criteria of AKI Risk (R), Injury (I), or Failure (F). Biomarker include urinary neutophil gelatinase-associated lipocalin (uNGAL), serum NGAL (sNGAL), urine liver-type fatty acid binding protein (uL-FABP), and urinary alpha-glutathione S-transferase (u-αGST), urinary glutathione S-transferase P (u-IIGST), and urinary cystatin-C (uCy-c), prior to surgery (0 hr), six hours after beginning CPB-assisted surgery (6 hr), and 24 hours after CPB-assisted surgery.

| | | | | | | RIFLE R | | | |
|---|---|---|---|---|---|---|---|---|---|
| | Mean | SD | Median | Q1 | Q3 | AUC | SE | 95% Low | 95% High |
| uN-gal 0 hr | 59.27 | 98.98 | 19.79 | 6.13 | 65.18 | | | | |
| uN-gal/uCr 0 hr | 114.60 | 315.87 | 23.80 | 7.68 | 87.34 | | | | |
| uN-gal 6 hr | 692.29 | 1721.20 | 194.24 | 63.52 | 592.92 | 0.71 | 0.06 | 0.59 | 0.83 |
| uN-gal/uCr 6 hr | 3460.62 | 5428.01 | 1234.08 | 374.32 | 4308.10 | 0.73 | 0.07 | 0.60 | 0.86 |
| ΔuN-gal/uCr 6 hr | 3346.01 | 5438.29 | 1018.02 | 325.29 | 4305.53 | 0.74 | 0.06 | 0.61 | 0.87 |
| uN-gal 24 hr | 318.12 | 766.61 | 85.34 | 37.00 | 231.68 | 0.66 | 0.07 | 0.53 | 0.78 |
| uN-gal/uCr 24 hr | 575.86 | 1572.94 | 96.33 | 41.05 | 284.69 | 0.70 | 0.06 | 0.58 | 0.82 |
| Δ uN-gal/uCr 24 hr | 461.26 | 1596.29 | 42.81 | 0.07 | 185.21 | 0.80 | 0.05 | 0.71 | 0.89 |
| uL-FAB 0 hr | 5.51 | 14.42 | 1.05 | 0.60 | 3.10 | | | | |
| uL-FAB/uCr 0 hr | 57.44 | 492.65 | 1.58 | 0.68 | 3.23 | | | | |
| UL-FAB 6 hr | 167.59 | 655.59 | 27.22 | 4.35 | 105.90 | 0.69 | 0.06 | 0.57 | 0.81 |
| uL-FAB/uCr 6 hr | 1353.01 | 6345.90 | 213.79 | 35.52 | 566.29 | 0.67 | 0.06 | 0.55 | 0.80 |
| Δ uL-FAB/uCr 6 hr | 1295.57 | 6375.23 | 190.40 | 25.36 | 549.77 | 0.67 | 0.06 | 0.55 | 0.80 |
| UL-FAB 24 hr | 62.53 | 205.21 | 12.60 | 6.39 | 32.89 | 0.56 | 0.07 | 0.42 | 0.71 |
| uL-FAB/uCr 24 hr | 273.12 | 1456.69 | 12.38 | 7.24 | 27.41 | 0.64 | 0.07 | 0.51 | 0.78 |
| Δ uL-FAB/uCr 24 hr | 215.68 | 1546.75 | 9.17 | 4.60 | 24.03 | 0.64 | 0.07 | 0.51 | 0.78 |
| u-α GST 0 hr | 7.58 | 7.27 | 5.00 | 2.40 | 10.60 | | | | |
| u-α GST/uCr 0 hr | 15.44 | 32.20 | 6.96 | 2.47 | 18.13 | | | | |
| u-α GST 6 hr | 37.13 | 243.09 | 6.40 | 2.60 | 13.00 | 0.60 | 0.07 | 0.46 | 0.74 |
| u-α GST/uCr 6 hr | 227.77 | 827.60 | 48.13 | 13.11 | 105.41 | 0.59 | 0.08 | 0.44 | 0.74 |
| Δu- α GST/uCr 6 hr | 212.33 | 828.72 | 35.45 | 4.02 | 96.34 | 0.62 | 0.07 | 0.49 | 0.76 |
| u-α GST 24 hr | 10.56 | 16.35 | 6.80 | 2.80 | 11.80 | 0.42 | 0.07 | 0.29 | 0.56 |
| u-α GST/Cr 24 hr | 20.79 | 51.11 | 6.57 | 2.75 | 16.89 | 0.48 | 0.07 | 0.34 | 0.62 |
| u-n GST 0 hr | 20.87 | 32.05 | 9.40 | 4.20 | 21.60 | | | | |
| u-n GST/uCr 0 hr | 35.57 | 83.17 | 12.72 | 5.48 | 25.51 | | | | |
| u-n GST 6 hr | 77.70 | 113.28 | 34.00 | 6.60 | 75.00 | 0.71 | 0.07 | 0.57 | 0.85 |
| n GST/Cr 6 | 578.34 | 1058.17 | 169.76 | 66.67 | 416.92 | 0.69 | 0.07 | 0.55 | 0.83 |
| Δ u-n GST/uCr 6 hr | 541.31 | 1063.73 | 141.71 | 44.91 | 407.64 | 0.71 | 0.07 | 0.59 | 0.84 |
| u-n GST 24 hr | 40.35 | 51.27 | 26.40 | 10.00 | 54.65 | 0.43 | 0.07 | 0.28 | 0.57 |
| u-n GST/uCr 24 hr | 127.40 | 501.97 | 28.66 | 12.71 | 56.73 | 0.48 | 0.07 | 0.33 | 0.62 |
| Δ u-n GST/uCr 24 hr | 90.51 | 511.95 | 10.73 | -4.19 | 37.41 | 0.59 | 0.06 | 0.46 | 0.71 |
| uCy-c 0 hr | 1.25 | 0.31 | 1.20 | 1.05 | 1.34 | | | | |

TABLE 7-continued

ROC AUC analysis of various biomarkers and their ratios to urinary creatinine (Cr) for discrimination of AKI by RIFLE criteria of AKI Risk (R), Injury (I), or Failure (F). Biomarker include urinary neutophil gelatinase-associated lipocalin (uNGAL), serum NGAL (sNGAL), urine liver-type fatty acid binding protein (uL-FABP), and urinary alpha-glutathione S-transferase (u-αGST), urinary glutathione S-transferase P (u-IIGST), and urinary cystatin-C (uCy-c), prior to surgery (0 hr), six hours after beginning CPB-assisted surgery (6 hr), and 24 hours after CPB-assisted surgery.

| | | | | | | | | | |
|---|---|---|---|---|---|---|---|---|---|
| uCy-c 6 hr | 1.26 | 0.31 | 1.21 | 1.06 | 1.40 | 0.69 | 0.06 | 0.56 | 0.82 |
| Δ uCy-c 6 hr | 0.01 | 0.21 | 0.00 | −0.12 | 0.14 | 0.68 | 0.08 | 0.53 | 0.82 |
| uCy-c 24 hr | 1.45 | 0.49 | 1.32 | 1.10 | 1.70 | 0.72 | 0.07 | 0.59 | 0.85 |
| Δ uCy-c 24 hr | 0.20 | 0.32 | 0.11 | −0.01 | 0.35 | 0.76 | 0.07 | 0.62 | 0.90 |
| serum N-gal 0 | 33.48 | 20.93 | 29.22 | 23.65 | 35.03 | | | | |
| serum N-gal 6 | 128.61 | 69.32 | 110.99 | 90.94 | 154.30 | 0.51 | 0.06 | 0.39 | 0.63 |
| Δ serum N-gal 6 | 95.22 | 71.85 | 76.12 | 55.67 | 124.59 | 0.47 | 0.06 | 0.35 | 0.60 |
| serum N-gal 24 | 37.18 | 16.51 | 33.19 | 27.69 | 40.59 | 0.53 | 0.07 | 0.40 | 0.66 |
| Δ serum N-gal 24 | 3.63 | 26.93 | 2.82 | −4.20 | 12.92 | 0.47 | 0.07 | 0.34 | 0.61 |

| | RIFLE I | | | | RIFLE F | | | |
|---|---|---|---|---|---|---|---|---|
| | AUC | SE | 95% Low | 95% High | AUC | SE | 95% Low | 95% High |
| uN-gal 0 hr | | | | | | | | |
| uN-gal/uCr 0 hr | | | | | | | | |
| uN-gal 6 hr | 0.59 | 0.08 | 0.44 | 0.74 | 0.52 | 0.09 | 0.35 | 0.69 |
| uN-gal/uCr 6 hr | 0.67 | 0.09 | 0.50 | 0.84 | 0.59 | 0.11 | 0.37 | 0.80 |
| ΔuN-gal/uCr 6 hr | 0.68 | 0.09 | 0.51 | 0.85 | 0.60 | 0.11 | 0.39 | 0.81 |
| uN-gal 24 hr | 0.64 | 0.08 | 0.48 | 0.80 | 0.64 | 0.10 | 0.45 | 0.83 |
| uN-gal/uCr 24 hr | 0.71 | 0.09 | 0.55 | 0.88 | 0.66 | 0.10 | 0.46 | 0.86 |
| Δ uN-gal/uCr 24 hr | 0.79 | 0.06 | 0.67 | 0.91 | 0.75 | 0.08 | 0.60 | 0.90 |
| uL-FAB 0 hr | | | | | | | | |
| uL-FAB/uCr 0 hr | | | | | | | | |
| UL-FAB 6 hr | 0.62 | 0.07 | 0.48 | 0.77 | 0.61 | 0.08 | 0.45 | 0.78 |
| uL-FAB/uCr 6 hr | 0.66 | 0.08 | 0.50 | 0.82 | 0.63 | 0.10 | 0.43 | 0.83 |
| Δ uL-FAB/uCr 6 hr | 0.66 | 0.08 | 0.50 | 0.82 | 0.63 | 0.10 | 0.43 | 0.83 |
| UL-FAB 24 hr | 0.43 | 0.10 | 0.23 | 0.63 | 0.54 | 0.11 | 0.31 | 0.76 |
| uL-FAB/uCr 24 hr | 0.55 | 0.10 | 0.37 | 0.74 | 0.59 | 0.11 | 0.37 | 0.81 |
| Δ uL-FAB/uCr 24 hr | 0.53 | 0.10 | 0.33 | 0.73 | 0.54 | 0.13 | 0.29 | 0.78 |
| u-α GST 0 hr | | | | | | | | |
| u-α GST/uCr 0 hr | | | | | | | | |
| u-α GST 6 hr | 0.59 | 0.09 | 0.41 | 0.77 | 0.58 | 0.11 | 0.37 | 0.79 |
| u-α GST/uCr 6 hr | 0.63 | 0.10 | 0.44 | 0.81 | 0.61 | 0.12 | 0.36 | 0.85 |
| Δu- α GST/uCr 6 hr | 0.65 | 0.09 | 0.46 | 0.83 | 0.62 | 0.12 | 0.38 | 0.85 |
| u-α GST 24 hr | 0.32 | 0.08 | 0.17 | 0.47 | 0.39 | 0.09 | 0.20 | 0.57 |
| u-α GST/Cr 24 hr | 0.42 | 0.09 | 0.25 | 0.59 | 0.48 | 0.11 | 0.27 | 0.68 |
| u-n GST 0 hr | | | | | | | | |
| u-n GST/uCr 0 hr | | | | | | | | |
| u-n GST 6 hr | 0.59 | 0.09 | 0.41 | 0.76 | 0.60 | 0.09 | 0.42 | 0.78 |
| n GST/Cr 6 | 0.60 | 0.09 | 0.41 | 0.78 | 0.59 | 0.11 | 0.38 | 0.81 |
| Δ u-n GST/uCr 6 hr | 0.63 | 0.09 | 0.46 | 0.80 | 0.63 | 0.10 | 0.44 | 0.82 |
| u-n GST 24 hr | 0.41 | 0.09 | 0.24 | 0.58 | 0.51 | 0.09 | 0.32 | 0.69 |
| u-n GST/uCr 24 hr | 0.56 | 0.09 | 0.38 | 0.74 | 0.61 | 0.09 | 0.43 | 0.78 |
| Δ u-n GST/uCr 24 hr | 0.47 | 0.08 | 0.32 | 0.62 | 0.47 | 0.10 | 0.28 | 0.66 |
| uCy-c 0 hr | | | | | | | | |
| uCy-c 6 hr | 0.65 | 0.08 | 0.51 | 0.79 | 0.69 | 0.07 | 0.54 | 0.83 |
| Δ uCy-c 6 hr | 0.53 | 0.10 | 0.34 | 0.72 | 0.56 | 0.12 | 0.33 | 0.80 |
| uCy-c 24 hr | 0.80 | 0.08 | 0.63 | 0.96 | 0.83 | 0.08 | 0.67 | 0.98 |
| Δ uCy-c 24 hr | 0.79 | 0.09 | 0.61 | 0.96 | 0.81 | 0.09 | 0.63 | 0.99 |
| serum N-gal 0 | | | | | | | | |
| serum N-gal 6 | 0.45 | 0.08 | 0.29 | 0.60 | 0.36 | 0.08 | 0.20 | 0.51 |
| Δ serum N-gal 6 | 0.45 | 0.08 | 0.30 | 0.60 | 0.37 | 0.08 | 0.22 | 0.52 |
| serum N-gal 24 | 0.47 | 0.08 | 0.31 | 0.63 | 0.50 | 0.09 | 0.32 | 0.68 |
| Δ serum N-gal 24 | 0.48 | 0.08 | 0.32 | 0.64 | 0.51 | 0.10 | 0.32 | 0.70 |

TABLE 8

Characteristics of patients developing AKI compared with those who did not develop AKI

| Variables | All Patients | | | Excluding Patients With Preoperative CKD | | |
|---|---|---|---|---|---|---|
| | AKI<br>N = 9 | No AKI<br>N = 91 | P value | AKI<br>N = 5 | No AKI<br>N = 69 | P value |
| Age, y | 74 (70-77) | 67 (56-73) | 0.015 | 75 (73-84) | 65 (55-72) | 0.003 |
| Female, n | 2 (22.2%) | 31 (34.1%) | 0.47 | 1 (20.0%) | 19 (27.5%) | >0.99 |
| Preoperative CKD, n | 4 (44.5%) | 22 (24.2%) | 0.23 | — | — | — |
| LVEF <35%, n | 3 (33.3%) | 8 (8.8%) | 0.06 | 1 (20.0%) | 6 (8.7%) | 0.40 |
| Preoperative eGFR, mL/min/1.73 m$^2$ | 61 (52-91) | 74 (62-88) | 0.58 | 86 (72-100) | 80 (70-92) | 0.52 |
| Arterial hypertension | 8 (88.9%) | 65 (71.4%) | 0.26 | 5 (100.0%) | 48 (69.6%) | 0.31 |
| COPD | 3 (33.3%) | 8 (8.8%) | 0.025 | 2 (40.0%) | 6 (8.7%) | 0.087 |
| Diabetes mellitus, n | 3 (33.3%) | 17 (18.7%) | 0.38 | 0 (0.0%) | 12 (17.4%) | 0.58 |
| PVD, n | 4 (44.5%) | 17 (18.7%) | 0.09 | 2 (40.0%) | 11 (15.9%) | 0.21 |
| Atrial fibrillation | 6 (66.7%) | 25 (27.5%) | 0.015 | 4 (80.0%) | 18 (26.1%) | 0.025 |

AKI, acute kidney disease; AKI defined as RIFLE class R or worse including serum creatinine increase and urine output decrease. Diabetes mellitus defined as diabetes on medication (insulin or oral antidiabetics). CKD, chronic kidney disease; COPD, chronic obstructive pulmonary disease; eGFR, estimated glomerular filtration rate; LVEF, left ventricular ejection fraction; PVD, peripheral vascular disease. Median (25$^{th}$ to 75$^{th}$ percentiles).

TABLE 9

Interventions and outcomes

| | All Patients | | | Excluding Patients With Preoperative CKD | | |
|---|---|---|---|---|---|---|
| CABG surgery, n | 2 (22.2%) | 17 (18.7%) | 0.68 | 1 (20.0%) | 13 (18.8%) | >0.99 |
| Valve surgery, n | 4 (44.5%) | 46 (50.5%) | >0.99 | 2 (40.0%) | 37 (53.6%) | 0.66 |
| CABG and valve surgery, n | 3 (33.3%) | 21 (23.1%) | 0.68 | 2 (40.0%) | 14 (20.3%) | 0.29 |
| Thoracic aortic surgery, n | 0 (0.0%) | 7 (7.7%) | >0.99 | 0 (0.0%) | 5 (7.3%) | >0.99 |

| Variables | AKI<br>N = 9 | No AKI<br>N = 91 | P value | AKI<br>N = 5 | No AKI<br>N = 69 | P value |
|---|---|---|---|---|---|---|
| Previous cardiothoracic surgery, n | 2 (22.2%) | 26 (28.6%) | >0.99 | 1 (20.0%) | 23 (33.3%) | >0.99 |
| Fluid balance, mL* | 4980 (3000-16200) | 3100 (1690-4660) | 0.035 | 4920 (450-16200) | 3100 (1260-4800) | 0.40 |
| Furosemide, n* | 9 (100%) | 84 (92.3%) | 0.39 | 5 (100.0%) | 63 (91.3%) | >0.99 |
| Furosemide, mg* | 130 (60-460) | 50 (20-90) | 0.003 | 160 (35-672) | 45 (20-70) | 0.05 |
| Vasopressor use, n* | 7 (77.8%) | 65 (71.4%) | 0.69 | 5 (100.0%) | 49 (71.0%) | 0.32 |
| Inotrope use, n* | 8 (88.9%) | 51 (63.7%) | 0.13 | 4 (80.0%) | 45 (65.2%) | 0.66 |
| Blood transfusion, n* | 8 (88.9%) | 52 (57.1%) | 0.06 | 4 (80.0%) | 39 (56.5%) | 0.39 |
| Blood transfusion, mL* | 1000 (500-6380) | 500 (0-500) | 0.005 | 1250 (250-6800) | 250 (0-500) | 0.048 |
| LOS In hospital, days | 14 (8-19) | 9 (7-14) | 0.024 | 14 (8-19) | 9 (7-14) | 0.48 |
| Need for RRT, n | 3 (33.3%) | 2 (2.2%) | 0.005 | 2 (40.0%) | 0 (0.0%) | 0.004 |
| Duratian of bypass, min | 125 (100-172) | 119 (91-158) | 0.62 | 109 (80-146) | 119 (90-156) | 0.57 |
| Hospital mortality, n | 3 (33.3%) | 0 (0%) | 0.001 | 1 (20.0%) | 0. (0.0%) | 0.068 |

AKI, acute kidney disease; AKI defined as RIFLE class R or worse including serum creatinine increase and urine output decrease. CABG; coronary artery bypass grafting; LOS, length of stay; RRT, renal replacement therapy. Median (25$^{th}$ to 75$^{th}$ percentiles).
*Including intraoperative and 48 hrs postoperative values.

TABLE 10

Peri-operative hepcidin indices

| | All Patients | | | Excluding Patients With Preoperative CKD | | |
|---|---|---|---|---|---|---|
| | No AKI<br>N = 91 | AKI<br>N = 9 | P value | No AKI<br>N = 69 | AKI<br>N = 5 | P value |
| uHep/uCr, ng/mg | | | | | | |
| Baseline | 308 (122-583) | 120 (34-295) | 0.07 | 309 (143-570) | 164 (100-633) | 0.60 |
| 6 hours after CPB start | 5175 (2086-9539) | 1229 (314-2379) | <0.001 | 5402 (2100-9300) | 1400 (639-2379) | 0.009 |
| 24 hours after CPB start* | 3255 (1576-6652) | 1345 (537-3583) | 0.07 | 3143 (1798-6585) | 1345 (971-3362) | 0.06 |
| Friedman test | <0.001 | 0.005 | | <0.001 | 0.11 | |
| uCr, mg/mL | | | | | | |
| Baseline | 1.14 (0.57-1.74) | 0.92 (0.51-1.83) | 0.52 | 1.28 (0.60-1.96) | 1.66 (0.78-2.10) | 0.71 |
| 6 hours after CPB start | 0.19 (0.10-0.28) | 0.21 (0.10-0.30) | 0.84 | 0.19 (0.11-0.28) | 0.21 (0.12-0.30) | 0.97 |
| 24 hours after CPB start* | 0.46 (0.24-0.71) | 0.22 (0.12-0.29) | 0.008 | 0.52 (0.29-0.73) | 0.22 (0.18-0.37) | 0.022 |
| Friedman test | <0.001 | 0.030 | | <0.001 | 0.17 | |
| uHep/uCr:pHep ratio | | | | | | |
| Baseline | 2.6 (1.2-4.9) | 1.1 (0.2-5.6) | 0.18 | 2.8 (1.2-4.8) | 4.6 (1.6-8.4) | 0.41 |
| 6 hours after CPB start | 3.1 (1.5-5.3) | 1.0 (0.2-3.1) | 0.047 | 3.6 (1.9-5.9) | 3.0 (1.0-46.7) | 0.59 |

TABLE 10-continued

Peri-operative hepcidin indices

| | All Patients | | | Excluding Patients With Preoperative CKD | | |
|---|---|---|---|---|---|---|
| | No AKI N = 91 | AKI N = 9 | P value | No AKI N = 69 | AKI N = 5 | P value |
| 24 hours after CPB start* | 6.9 (2.0-13.3) | 1.2 (0.6-2.4) | 0.011 | 8.2 (3.8-15.1) | 2.3 (0.8-11.6) | 0.11 |
| Friedman test | <0.001 | 0.69 | | <0.001 | 0.74 | |
| FE hepcidin, % | | | | | | |
| Baseline | 2.4 (1.5-4.1) | 1.7 (0.7-2.5) | 0.17 | 2.3 (1.5-2.9) | 2.5 (1.8-4.7) | 0.58 |
| 6 hours after CPB start | 22.1 (12.2-30.0) | 8.3 (1.7-19.5) | 0.005 | 22.0 (15.1-30.5) | 16.3 (3.6-22.5) | 0.19 |
| 24 hours after CPB start* | 14.7 (9.5-25.2) | 8.1 (4.5-46.5) | 0.35 | 15.3 (9.9-25.2) | 8.1 (5.1-55.7) | 0.60 |

AKI, acute kidney disease; AKI defined as RIFLE class R or worse including serum creatinine increase and urine output decrease. CPB; cardiopulmonary bypass. Median ($25^{th}$ to $75^{th}$ percentiles).
*Values at 24 hours after CPB start refer to 89 patients without AKI and 9 patients with AKI.

TABLE 11

Predictive values of hepcidin for protection from AKI (=NO AKI) excluding patients with preoperative CKD

| | AUC-ROC (95% CI) | Sensitivity | Specificity | Cut off |
|---|---|---|---|---|
| uHep, ng/mL | | | | |
| 6 hours after CPB start | 0.81 (0.67-0.96) | 62.3% | 100.0% | >545 |
| 24 hours after CPB start* | 0.83 (0.74-0.92) | 79.7% | 100.0% | >475 |
| uHep/uCr, ng/mg | | | | |
| 6 hours after CPB start | 0.87 (0.75-0.99) | 70.0% | 100.0% | >2820 |
| 24 hours after CPB start* | 0.75 (0.57-0.94) | 76.5% | 80.0% | >1762 |
| pHep, ng/mL | | | | |
| 6 hours after CPB start | 0.70 (0.46-0.98) | 69.0% | 80.0% | >175 |
| 24 hours after CPB start* | 0.54 (0.23-0.86) | N/A | N/A | N/A |

AKI, acute kidney disease; AKI defined as RIFLE class R or worse including serum creatinine increase and urine output decrease. CKD, chronic kidney disease; CPB; cardiopulmonary bypass; N/A, values not presented for AUC-ROC <0.6.
*Values at 24 hours after CPB start refer to 89 patients without AKI and 9 patients with AKI.

TABLE 12

Multivariate logistic regression analysis (all patients) of risk factors and biomarkere at 6 hours after CPB start for the prediction of NO AKI.

| | Model 0 ($R^2$ = 0.42) | | Model 1 ($R^2$ = 0.63) | | Model 2 ($R^2$ = 0.43) | | Model 3 ($R^2$ = 0.50) | |
|---|---|---|---|---|---|---|---|---|
| | Regression coefficient(B) (SE) | P | Regression coefficient(B) (SE) | P | Regression coefficient(B) (SE) | P | Regression coefficient(B) (SE) | P |
| Age, y. | −0.2 (0.1) | 0.015 | −0.2 (0.1) | 0.06 | −0.1 (0.1) | 0.06 | −0.2 (0.1) | 0.036 |
| LVEF <35% | −2.9 (1.1) | 0.009 | −4.1 (1.6) | 0.008 | −2.7 (1.1) | 0.011 | −3.0 (1.2) | 0.010 |
| COPD | −2.2 (1.0) | 0.036 | −2.4 (1.3) | 0.06 | −2.0 (1.0) | 0.044 | −2.5 (1.1) | 0.026 |
| log uHep/uCr, ng/mg | | | 2.9 (1.1) | 0.011 | | | | |
| log uHep, ng/mL | | | | | 1.2 (0.7) | 0.09 | | |
| log pHep, ng/mL | | | | | | | 2.7 (2.5) | 0.56 |

Variables tested on univariate relation with incidence of AKI included all variables displayed in Table 1, type and duration of surgery and renal biomarkers at 6 hours after start of CPB. Multivariate logistic regression analysis included relevant variables for (no) AKI with univariate P value <0.1 (age, atrial fibrillation, LVEF <35%, COPD, PVD). Variables were presented in model 0 if their multivariate P value was <0.05 (age, LVEF <35%, COPD).
We included each biomarker one after another (model 1-3) into multivariate regression analysis to exclude interaction.
LVEF, left ventricular ejection fraction; COPD, chronic obstructive pulmonary disease; PVD, peripheral vascular disease.

Unless otherwise defined, all technical and scientific terms used here have the same meaning as commonly understood by those skilled in the art to which this invention belongs.

The inventions illustratively described here may suitably be practiced in the absence of any element or elements, limitation or limitations, not specifically disclosed here. Thus, for example, the terms "comprising," "including," "containing," etc. shall be read expansively and without limitation. Additionally, the terms and expressions employed here have been used as terms of description and not of limitation, and there is no intention in the use of such terms and expressions of excluding any equivalents of the features shown and described or portions thereof. It is recognized that various modifications are possible within the scope of the invention claimed.

Thus, it should be understood that although the present invention has been specifically disclosed by preferred embodiments and optional features, modification, improvement, and variation of the inventions disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically here. Each of the narrower species and subgeneric groupings falling within the generic disclosure also form part of the invention. This includes the generic description of the invention with a proviso or negative limitation removing any subject matter from the genus, regardless of whether or not the excised material is specifically recited here.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned here are expressly incorporated by reference in their entirety, to the same extent as if each were incorporated by reference individually. In case of conflict, the present specification, including definitions, will control.

Other embodiments are set forth within the following claims.

What is claimed is:

1. A method for diagnosing and treating acute kidney injury (AKI) in a patient following an event likely to cause kidney injury and/or failure in the patient, comprising:
   (A) obtaining a urine or plasma sample from a patient;
   (B) measuring levels for urine or plasma hepcidin, and measuring levels of creatinine in the urine or plasma sample of said patient following said event; and
   (C) diagnosing the patient with predicted risk of AKI using a ratio of (uHep/uCr):pHep, calculated by dividing a ratio of urine hepcidin to urinary creatinine (uHep/uCr) by plasma hepicidin (pHep), wherein a lack of an increase in the (uHep/uCr):pHep ratio at about 6 hours compared to the ratio at about 24 hours following the event is indicative of an increased risk for AKI; and
   (D) administering an effective amount of sodium bicarbonate to the patient diagnosed with increased risk for AKI as an intervention treatment by intravenous loading of sodium bicarbonate followed by a continuous infusion of sodium bicarbonate, wherein the event is cardiopulmonary bypass (CPB) surgery.

2. The method of claim 1, comprising measuring serum hepcidin (sHep) and serum creatinine (sCr) and also measuring serum NGAL (sNGAL) in said patient following said event, and then using the kinetics of change in sHep and sNGAL/sCr to diagnose the patient with predicted risk of AKI.

3. The method of claim 1, comprising measuring serum hepcidin (sHep) and urinary creatinine (uCr) and also measuring urinary NGAL (uNGAL) in said patient following said event, and then using the kinetics of change of sHep and uNGAL/uCr to diagnose the patient with predicted risk of AKI.

4. The method of claim 1, comprising measuring levels of urine hepcidin (uHep), urinary creatinine (uCr), serum creatinine (sCr) and serum NGAL (sNGAL) in said patient following said event, and then using the kinetics of sNGAL/sCr and uHep/uCr to diagnose the patient with predicted risk of AKI.

5. The method of claim 1, wherein the ratio of uHep/uCr measured at about 24 hours post initiation of cardiopulmonary bypass (CPB) is used to diagnose the patient with predicted risk of AKI.

6. The method of claim 1, wherein no change or a decrease in the ratio of uHep/uCr between about 6 hours and about 24 hours post initiation CPB is used to diagnose the patient with predicted risk of AKI.

7. The method of claim 1, wherein an increase in the ratio of uHep/uCr of between about 6 hours and about 24 post initiation of CPB of <35% is used to diagnose the patient with predicted risk of AKI.

8. The method of claim 1, wherein urinary NGAL (uNGAL) also is measured, and wherein the ratio of the change in uNGAL/uCr from post initiation of CPB surgery to about 24 hours to the change in uHep/uCr from post initiation of CPB surgery to 24 hours is used to diagnose the patient with predicted risk of AKI.

9. The method of claim 1, wherein urinary NGAL (uNGAL) also is measured, and wherein a weighted linear combination of uHep/uCr and uNGAL/uCr is used with Receiver-operating characteristic (ROC) area-under-the-curve analysis to diagnose the patient with predicted risk of AKI.

10. The method of claim 1, further comprising administering an intervention treatment to the patient selected from the group consisting of dialysis, continuous hemofiltration, and administering a drug that inhibits local inflammation and tissue damage.

11. The method of claim 1, wherein (C) comprises using kinetics of the change in said ratio to diagnose the patient with predicted risk of AKI.

12. The method of claim 11, further comprising obtaining levels of urinary NGAL in said patient following said event and using the ratio of urinary NGAL to urinary creatinine to diagnose the patient with predicted risk of AKI.

13. The method of claim 1, wherein an increase in the ratio of uHep/uCr between about 6 hours and about 24 post initiation of CPB of >25% is used to diagnose the patient with no or low risk of AKI.

14. The method of claim 13, wherein an increase in the ratio of uHep/uCr between about 6 hours and about 24 post initiation of cardiopulmonary bypass (CPB) of >35% is used to diagnose the patient with no risk of AKI.

* * * * *